(12) United States Patent
Takahashi et al.

(10) Patent No.: US 10,335,503 B2
(45) Date of Patent: Jul. 2, 2019

(54) COMPOUND THAT SPECIFICALLY BINDS TO AMPA RECEPTOR

(71) Applicant: Public University Corporation Yokohama City University, Yokohama-Shi Kanagawa (JP)

(72) Inventors: Takuya Takahashi, Yokohama (JP); Tomoyuki Miyazaki, Yokohama (JP); Tetsuya Suhara, Chiba (JP); Makoto Higuchi, Chiba (JP); Meiei Cho, Chiba (JP)

(73) Assignee: Public University Corporation Yokohama City University, Yokohama-Shi, Kanagawa (JP)

( * ) Notice: Subject to any disclaimer, the term of this patent is extended or adjusted under 35 U.S.C. 154(b) by 0 days.

(21) Appl. No.: 15/741,965

(22) PCT Filed: Jul. 5, 2016

(86) PCT No.: PCT/JP2016/069896
§ 371 (c)(1),
(2) Date: Jan. 4, 2018

(87) PCT Pub. No.: WO2017/006931
PCT Pub. Date: Jan. 12, 2017

(65) Prior Publication Data
US 2018/0200391 A1   Jul. 19, 2018

(30) Foreign Application Priority Data

Jul. 6, 2015  (JP) ................................. 2015-135124

(51) Int. Cl.
| A61K 51/00 | (2006.01) |
| A61M 36/14 | (2006.01) |
| A61K 51/04 | (2006.01) |
| C07C 319/20 | (2006.01) |
| C07C 323/49 | (2006.01) |
| C07F 7/22 | (2006.01) |
| C07B 59/00 | (2006.01) |

(52) U.S. Cl.
CPC .............. *A61K 51/04* (2013.01); *A61K 51/00* (2013.01); *C07B 59/001* (2013.01); *C07B 59/004* (2013.01); *C07C 319/20* (2013.01); *C07C 323/49* (2013.01); *C07F 7/22* (2013.01); *C07B 2200/05* (2013.01)

(58) Field of Classification Search
CPC ...... A61K 51/04; A61K 51/00; C07B 59/001; C07B 2200/05
USPC ....................................................... 424/1.89
See application file for complete search history.

(56) References Cited

U.S. PATENT DOCUMENTS

| 5,189,211 A | 2/1993 | Sato et al. |
| 5,955,505 A | 9/1999 | Takeo et al. |
| 6,949,571 B2 | 9/2005 | Nagato et al. |
| 7,476,668 B2 | 1/2009 | Graindorge et al. |
| 2004/0023973 A1 | 2/2004 | Nagato et al. |
| 2007/0004709 A1 | 1/2007 | Francotte et al. |
| 2012/0230914 A1 | 9/2012 | Watanabe et al. |

FOREIGN PATENT DOCUMENTS

| JP | 4-364158 A | 12/1992 |
| JP | 2006-525292 A | 11/2006 |
| JP | 2010-202525 A | 9/2010 |
| JP | 2012-207021 A | 10/2012 |
| WO | WO 96/25926 A1 | 8/1996 |
| WO | WO 2011/002096 A1 | 1/2011 |
| WO | WO 2014/163210 A1 | 10/2014 |
| WO | WO 2015/066456 A1 | 5/2015 |

OTHER PUBLICATIONS

Ahmed et al., Molecular mechanism of flop selectivity and subsite recognition for an AMPA receptor allosteric modulator: structures of GluA2 and GluA3 in complexes with PEPA. Biochemistry. Apr. 6, 2010;49(13):2843-50.

(Continued)

*Primary Examiner* — Michael G. Hartley
*Assistant Examiner* — Sean R Donohue
(74) *Attorney, Agent, or Firm* — Wolf, Greenfield & Sacks, P.C.

(57) ABSTRACT

The present invention provides a compound represented by formula (I), a pharmaceutically acceptable salt thereof or a solvate thereof.

[Chem 1]

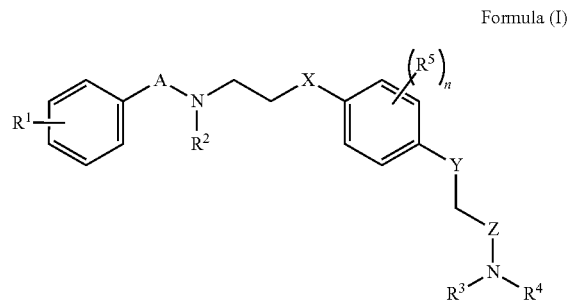

Formula (I)

(In the formula, each of A and Z independently represents CO, SO or $SO_2$; each of X and Y independently represents S or O; each of $R^1$-$R^4$ independently represents a hydrogen atom, an alkyl group, an alkenyl group, an alkynyl group or a halogen group; each $R^5$ independently represents an alkyl group, an alkenyl group, an alkynyl group or a halogen group; and n represents an integer of 0-4.) This compound is capable of specifically binding to an AMPA receptor, and shows extremely high brain uptake.

27 Claims, 5 Drawing Sheets

(56) References Cited

OTHER PUBLICATIONS

Arstad et al., Closing in on the AMPA receptor: Synthesis and evaluation of 2-acetyl-1-(4'-chlorophenyl)-6-methoxy-7-[11C]methoxy-1,2,3,4-tetrahydroisoquinoline as a potential PET tracer. Bioorg. Med. Chem. Jul. 15, 2006;14(14):4712-7.
Gao et al., Synthesis of carbon-11 and fluorine-18 labeled N-acetyl-l-aryl-6,7-dimethoxy-1,2,3,4-tetrahydroisoquinoline derivatives as new potential PET AMPA receptor ligands. Bioorg. Med. Chem. Lett. Apr. 15, 2006;16(8):2229-33.
International Search Report and Written Opinion dated Sep. 20, 2016 for Application No. PCT/JP2016/069896.
Langstrom et al., Endogenous compounds labeled with radionuclides of short half-life-some perspectives. J. Labelled Comp. Radiopharm. Mar.-Apr. 2013;56(3-4):251-62.
Sato et al., Synthesis and evaluation of novel fluorinated sulotroban-related sulfonamide derivatives as thromboxane A2 receptor antagonists. Eur. J. Med. Chem. 1995;30(5):403-14.
Extended European Search Report for European Application No. 16821400.5, dated Feb. 12, 2019.
Office Action for Korean Patent Application No. 10-2018-7003434, dated Mar. 4, 2019.

[Fig.1]
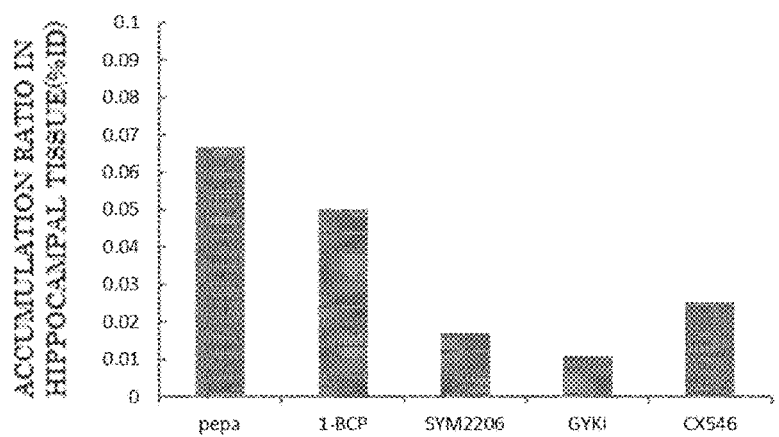
[Fig.2]
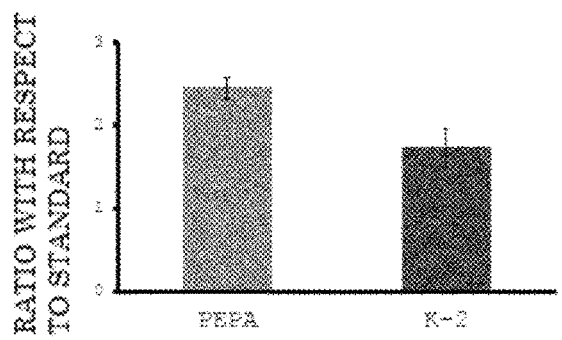
[Fig.3]
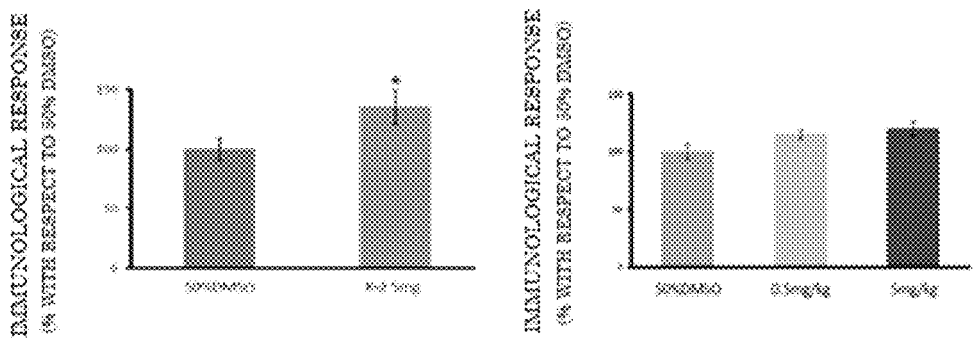

[Fig.4]
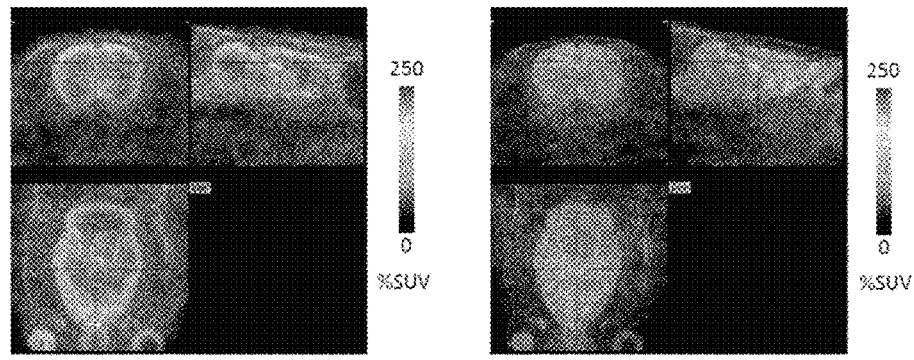
[Fig.5]
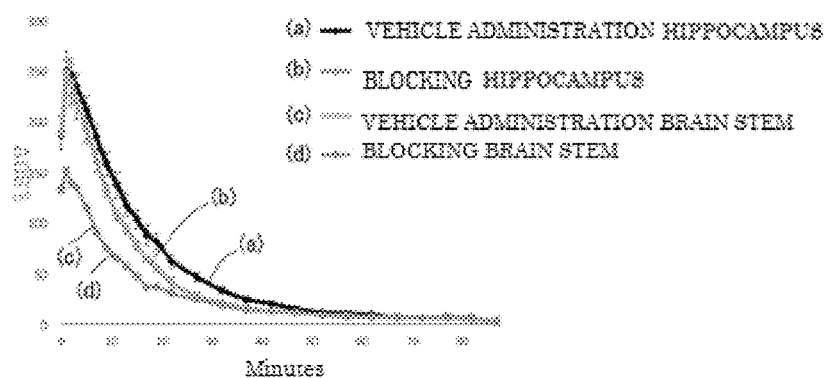
(a) — VEHICLE ADMINISTRATION HIPPOCAMPUS
(b) — BLOCKING HIPPOCAMPUS
(c) — VEHICLE ADMINISTRATION BRAIN STEM
(d) — BLOCKING BRAIN STEM
Minutes
[Fig.6]
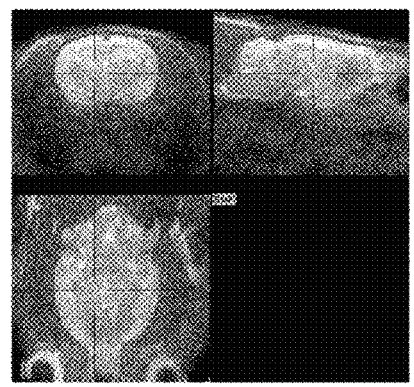

[Fig.7]
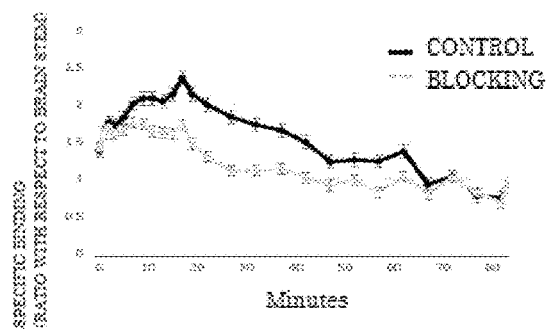
[Fig.8]
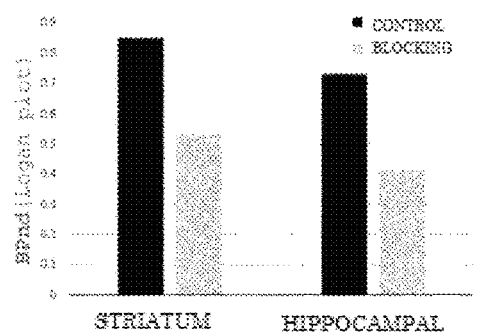
[Fig.9]
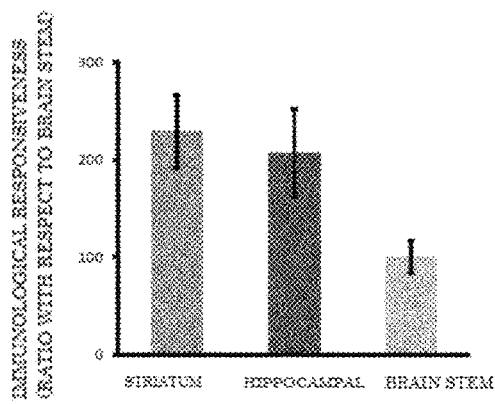

[Fig.10]
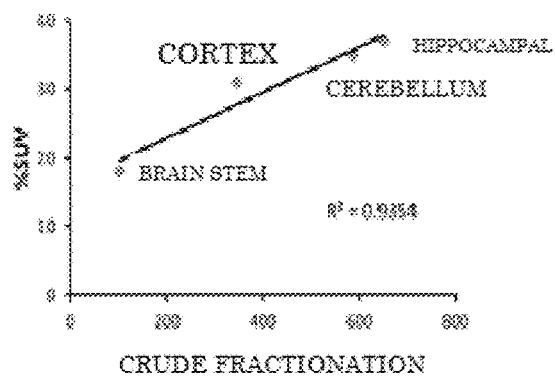
[Fig.11]
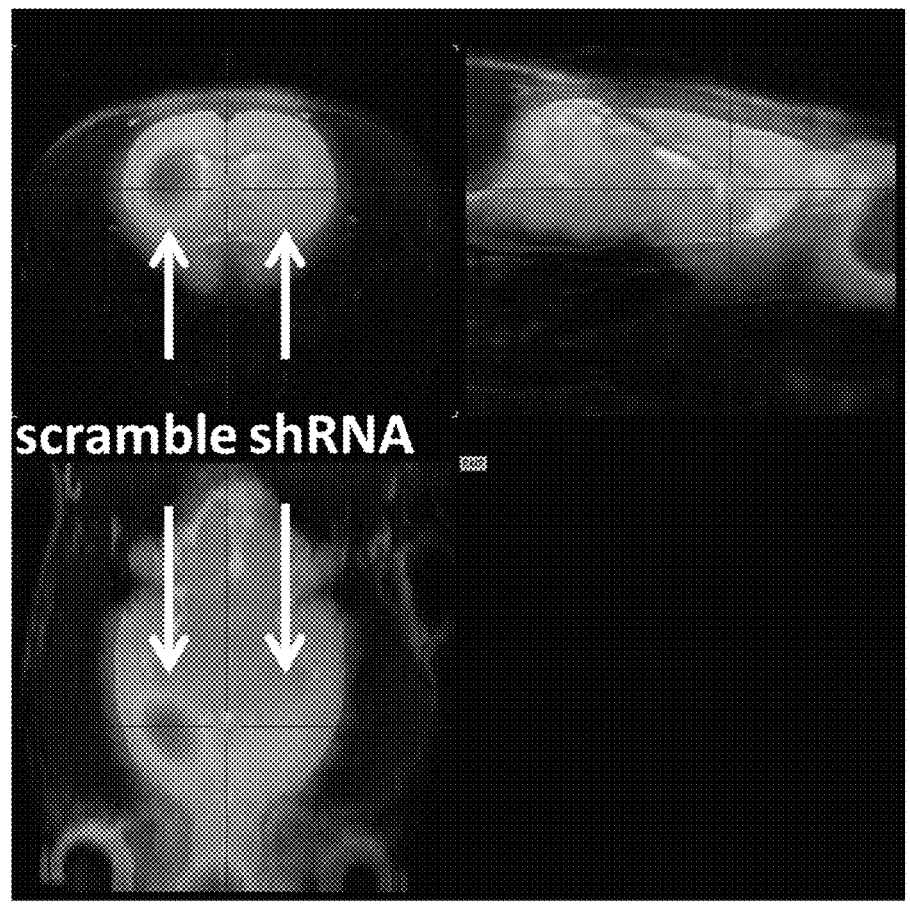

[Fig.12]
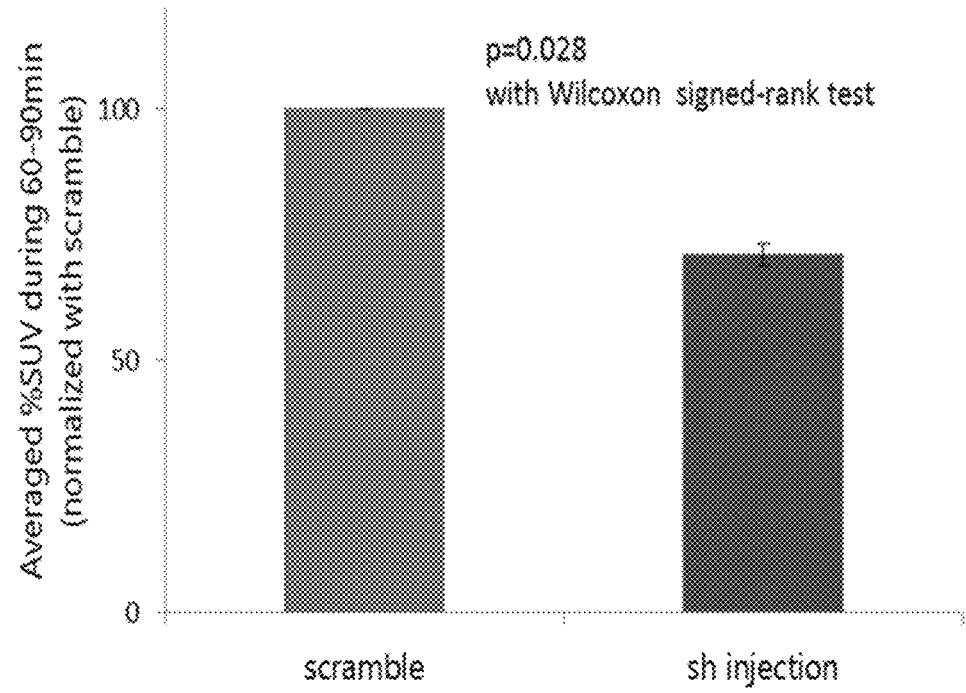

COMPOUND THAT SPECIFICALLY BINDS TO AMPA RECEPTOR

CROSS REFERENCE TO RELATED APPLICATIONS

This application is a National Stage filing under 35 U.S.C. § 371 of International PCT Application No. PCT/JP2016/069896, filed Jul. 5, 2016, which claims priority to Japanese Patent Application No. 2015-135124, filed Jul. 6, 2015, the entire contents of the aforementioned applications are hereby incorporated herein by reference.

TECHNICAL FIELD

The present invention relates to a novel compound that specifically binds to an α-amino-3-hydroxy-5-methyl-4-isoxazole-propionic acid (AMPA) receptor, a pharmaceutically acceptable salt thereof, and a solvate thereof, and a composition containing these compounds, a method for producing these compounds, and an intermediate used for producing these compounds.

BACKGROUND ART

It is known that AMPA receptors widely distribute in the central nervous system and involve in learning, memory, neurological degeneration, cell death, and the like. In recent years, researches related to treatment for psychiatric and neurological diseases using AMPA receptors as targets (Patent Documents 1 to 3). In order to examine the relation between the AMPA receptors and these diseases, it is required to evaluate the expression level and the distribution of AMPA receptors in the brain. However, there are various problems in that there is no choice but to use the postmortem brains at the present time in order to examine the expression level or the like of these AMPA receptors and comparison with an able-bodied person cannot be conducted.

A molecular imaging method, for example, positron emission tomography (PET) is a method capable of visualizing the behaviors of molecules in living subjects in vivo. In order to visualize the behaviors of AMPA receptors in living subjects in vivo, hitherto, some molecular probes have been synthesized (Non-Patent Documents 1 to 3). However, from the reasons that conventional molecular probes have insufficient specific binding to AMPA receptors and low brain uptake of the probes, these molecular probes are difficult to use for in vivo imaging of AMPA receptors. Therefore, there is a demand for development of a new compound that specifically binds to an AMPA receptor and exhibits a high accumulation in the brain.

Patent Document 1: Japanese Unexamined Patent Application, Publication No. 2012-207021
Patent Document 2: Japanese Unexamined Patent Application, Publication No. 2010-202525
Patent Document 3: Japanese Unexamined Patent Application (Translation of PCT Application), Publication No. 2006-525292
Non-Patent Document 1: Gao M et al., Synthesis of carbon-11 and fluorine-18 labeled N-acetyl-1-aryl-6,7-dimethoxy-1,2,3,4-tetrahydroisoquinoline derivatives as new potential PET AMPA receptor ligands., Bioorg. Med. Chem. Lett. 2006 Apr. 15; 16(8):2229-33.
Non-Patent Document 2: Langstrom B et al., Endogenous compounds labeled with radionuclides of short half-life-some perspectives., J. Labelled Comp. Radiopharm. 2013 March-April; 56(3-4): 251-62.
Non-Patent Document 3: Arstad E. et al., Closing in on the AMPA receptor: synthesis and evaluation of 2-acetyl-1-(4'-chlorophenyl)-6-methoxy-7-[11C]methoxy-1,2,3,4-tetrahydroisoquinoline as a potential PET tracer., Bioorg. Med. Chem. 2006 Jul. 15; 14(14):4712-7.

DISCLOSURE OF THE INVENTION

Problems to be Solved by the Invention

An object of the present invention is to provide a novel compound that specifically binds to an AMPA receptor and has high brain uptake. In particular, an object of the present invention is to provide a novel compound used for imaging an AMPA receptor in vivo.

Means for Solving the Problems

The present inventors have conducted intensive studies, and as a result, have succeeded in synthesizing a novel compound capable of specifically binding to an AMPA receptor. Furthermore, the present inventors have found based on a finding related to an interaction site between 2-[2,6-difluoro-4-({2-[(phenylsulfonyl)amino]ethyl}thio)phenoxy]acetamide and an AMPA receptor by crystal structure analysis (Biochemistry, 2010, Vol. 49, pp. 2843 to 2850), that a compound has a sulfonamide site (—SO₂N—) and an amide group (—CON—) at both ends thereof, and a substituent can be added to a nitrogen atom of the sulfonamide group without impairing the binding activity to the AMPA receptor so that accumulation property of the compound in the brain is improved. Therefore, according to the present invention, there is provided a compound represented by the following Formula (I), or a pharmaceutically acceptable salt or solvate thereof.

[Chem. 1]

Formula (I)

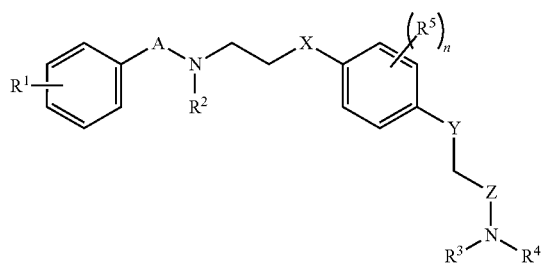

(in the formula,
each of A and Z independently represents CO, SO, or SO$_2$;
each of X and Y independently represents S or O;
each of R$^1$ to R$^4$ independently represents hydrogen, alkyl, alkenyl, alkynyl, or halo;
each R$^5$ independently represents alkyl, alkenyl, alkynyl, or halo; and
n represents an integer of 0 to 4.)

In an embodiment, in the compound represented by Formula (I), one or more atoms are a radioisotope of the atom or atoms.

Effects of the Invention

The compound of the present invention can specifically bind to an AMPA receptor and has extremely high brain uptake. In particular, the compound of the present invention can be used as a molecular probe, for example, a PET probe, and can image the AMPA receptor in living subjects in vivo. Further, the compound of the present invention is easily synthesized and can be obtained with a high yield.

BRIEF DESCRIPTION OF THE DRAWINGS

FIG. 1 is a graph showing accumulation ratios of various compounds in hippocampal tissues.

FIG. 2 is a graph showing a ratio of an AMPA current to a reference value after administration of PEPA or K-2.

FIG. 3 is a graph showing a change in the amount of an AMPA receptor when K-2 or a vehicle is administered to a living organism. Left diagram: An amount of the AMPA receptor presented on the surface of the cell membrane, Right diagram: A total amount of the AMPA receptor.

FIG. 4 is an in vivo PET image of a rat using radio-labeled K-2. Left diagram: A rat to which a vehicle is administered, Right diagram: A rat which is subjected to blocking by 0.5 mg/kg of non-radio-labeled K-2.

FIG. 5 shows time-activity curves (TAC) of K-2 of the hippocampus and the brain stem of a rat.

(a) Hippocampus after administration of the vehicle, (b) Hippocampus after blocking, (c) Brain stem after administration of the vehicle, and (d) Brain stem after blocking. In the graph, the line of (c) and the line of (d) overlap each other.

FIG. 6 is an in vivo PET image of a rat which is subjected to blocking by low-concentration (0.05 mg/kg) non-radio-labeled K-2.

FIG. 7 shows the TAC of specific binding using the brain stem as a control.

FIG. 8 is a graph in which specificity of radio-labeled K-2 in vivo is quantitatively determined. Left: Striatum, Right: Hippocampus. Black: A rat to which a vehicle is administered, Gray: A rat which is subjected to blocking.

FIG. 9 is a graph showing comparison of total expression level of an AMPA receptor in each brain region.

FIG. 10 is a graph showing a correlation between a biochemical expression level of an AMPA receptor in each brain region and a PET image value (% SUV).

FIG. 11 is an in vivo PET image of a rat to which shRNA is administered at both striatum sides. shRNA with respect to GluA1 to 3 (RNA that causes the protein of the AMPA receptor not to be expressed) is expressed in the left striatum of the same individual and scramble RNA (RNA that does not particularly have an effect) is expressed in the right striatum thereof.

FIG. 12 is a graph showing comparison of PET image values in the shRNA side and the scramble side of the rat to which shRNA is administered at both striatum sides.

PREFERRED MODE FOR CARRYING OUT THE INVENTION

1. Definitions

The term "alkyl" means a monovalent group that is produced when saturated aliphatic hydrocarbon misses one hydrogen atom. An alkyl has, for example, 1 to 15 ($C_1$-$C_{15}$) carbon atoms, and typically has 1 to 10 ($C_1$-$C_4$), 1 to 8 ($C_1$-$C_8$), 1 to 6 ($C_1$-$C_6$), 1 to 5 ($C_1$-$C_5$), 1 to 4 ($C_1$-$C_4$), 1 to 3 ($C_1$-$C_3$), 1 to 2 ($C_1$-$C_2$), or 2 to 6 ($C_2$-$C_6$) carbon atoms. An alkyl may be a straight chain or may be branched. Examples of alkyls include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, t-butyl, pentyl, isopentyl, neopentyl, and hexyl. An alkyl may be further substituted by an adequate substituent. The term "alkyl" may include an alkyl containing a radioisotope, for example, [$^{11}$C]alkyl.

The term "alkenyl" means an unsaturated aliphatic hydrocarbon group having at least one double bond. An alkenyl has, for example, 2 to 15 ($C_2$-$C_{15}$) carbon atoms, and typically has 2 to 10 ($C_2$-$C_{10}$), 2 to 8 ($C_2$-$C_8$), 2 to 6 ($C_2$-$C_6$), 2 to 5 ($C_2$-$C_5$), 2 to 4 ($C_2$-$C_4$), 2 to 3 ($C_2$-$C_3$), 3 to 6 ($C_3$-$C_6$), 3 to 8 ($C_3$-$C_8$), 4 to 6 ($C_4$-$C_8$), 4 to 7 ($C_4$-$C_7$), or 4 to 8 ($C_4$-$C_8$) carbon atoms. An alkenyl may be a straight chain or may be branched. Examples of alkenyls include, but are not limited to, specifically, vinyl (—CH=CH$_2$), allyl (—CH$_2$CH=CH$_2$), —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, 1,3-butadienyl (—CH=CH—CH=CH$_2$), and hepta-1,6-diene-4-yl (—CH$_2$—(CH$_2$CH=CH$_2$)$_2$). An alkenyl may be further substituted by an adequate substituent. The term "alkenyl" may include an alkenyl containing a radioisotope, for example, [$^{11}$C]alkenyl.

The term "alkynyl" means an unsaturated aliphatic hydrocarbon group having at least one triple bond. An alkynyl has, for example, 2 to 15 ($C_2$-$C_{15}$) carbon atoms, and typically has 2 to 10 ($C_2$-$C_{10}$), 2 to 8 ($C_2$-$C_8$), 2 to 6 ($C_2$-$C_6$), 2 to 5 ($C_2$-$C_5$), 2 to 4 ($C_2$-$C_4$), 2 to 3 ($C_2$-$C_3$), 3 to 6 ($C_3$-$C_6$), 3 to 8 ($C_3$-$C_8$), 4 to 6 ($C_4$-$C_8$), 4 to 7 ($C_4$-$C_7$), or 4 to 8 ($C_4$-$C_8$) carbon atoms. An alkynyl may be a straight chain or may be branched. Examples of alkynyl include, but are not limited to, ethynyl (—C≡CH), —C≡CH(CH$_3$), —C≡C(CH$_2$CH$_3$), —CH$_2$C≡CH, —CH$_2$C≡C(CH$_3$), and —CH$_2$C≡C(CH$_2$CH$_3$). An alkynyl may be further substituted by an adequate substituent. The term "alkynyl" may include an alkynyl containing a radioisotope, for example, [$^{11}$C]alkynyl.

The term "[$^{11}$C]alkyl" means an alkyl in which one or more carbon atoms in the carbon atoms constituting alkyl are $^{11}$C. Similarly, the term "[$^{11}$C]alkenyl" and the term "[$^{11}$C]alkynyl" mean an alkenyl in which one or more carbon atoms in the carbon atoms constituting alkenyl are $^{11}$C and an alkynyl in which one or more carbon atoms in the carbon atoms constituting alkynyl are $^{11}$C, respectively.

The term "halogen" or "halo" means fluoro (—F), chloro (—Cl), bromo (—Br), and iodine (—I).

The term "pharmaceutically acceptable salt" indicates a salt that is not harmful to mammals, particularly humans. Pharmaceutically acceptable salts can be formed using non-toxic acids or bases including inorganic acids or inorganic bases, or organic acids or organic bases. Examples of pharmaceutically acceptable salts include metal salts formed with aluminum, calcium, lithium, magnesium, potassium, sodium, zinc, and the like, and organic salts formed with lysine, N,N'-dibenzylethylenediamine, chloroprocaine, choline, diethanolamine, ethylenediamine, meglumine (N-methylglucamine), procaine, and the like. Further, pharmaceutically acceptable salts include acid-addition salts and base-addition salts.

The term "solvate" means a solvent-containing compound that is formed by association of one or a plurality of solvent molecules to the compounds of the present invention. Solvates include, for example, monosolvates, disolvates, trisolvates, and tetrasolvates. Further, solvates include hydrates.

2. Compound and Radio-Labeled Compound

The present invention provides a compound represented by the following Formula (I), or a pharmaceutically acceptable salt or solvate thereof.

[Chem. 2]

Formula (I)

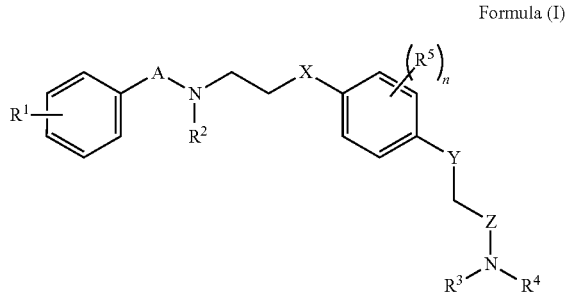

In the formula, each of A and Z independently represents CO, SO, or $SO_2$, and in the case of these groups, it is expected that the interaction between the groups and the AMPA receptor is exhibited. Among these, preferably, each of A and Z independently represents CO or $SO_2$, more preferably, A represents $SO_2$ and Z represents CO. Each of X and Y independently represents S or O, preferably, X represents S and Y represents O. Each of $R^1$ to $R^4$ independently represents hydrogen, alkyl, alkenyl, alkynyl, or halo. In an embodiment, all of $R^1$ to $R^4$ are not hydrogen, that is, at least one of $R^1$ to $R^4$ represents an element other than hydrogen. In an embodiment, $R^2$ represents alkyl. In another embodiment, $R^1$ represents alkyl or halo. $R^1$ can be located at any position of the ortho-position, the meta-position, and the para-position. Preferably, $R^1$ is located at the para-position. In still another embodiment, one of $R^3$ and $R^4$ represents hydrogen and the other one is alkyl. Each $R^5$ independently represents alkyl, alkenyl, alkynyl, or halo. Preferably, $R^5$ represents halo, particularly preferably fluoro. Further preferably, $R^5$ is located at both the ortho-positions with respect to the Y group (that is, both the meta-positions with respect to the X group).
n represents an integer of 0 to 4. Preferably, n is 2.

In still another embodiment, as a combination of respective substituents in the compound represented by Formula (I), a combination is preferable in which A represents $SO_2$, Z represents CO, X represents S, Y represents O, $R^2$ represents alkyl, $R^1$ represents hydrogen, alkyl, or halo, and in a case where $R^1$ represents alkyl or halo, $R^1$ is located at the para-position, one of $R^3$ and $R^4$ represents hydrogen and the other one is alkyl, each $R^5$ independently represents alkyl, alkenyl, alkynyl, or halo, and n represents an integer of 0 to 4.

In still another embodiment, as a combination of respective substituents in the compound represented by Formula (I), a combination is preferable in which A represents $SO_2$, Z represents CO, X represents S, Y represents O, $R^2$ represents alkyl, $R^1$ represents hydrogen, alkyl, or halo, and in a case where $R^1$ represents alkyl or halo, $R^1$ is located at the para-position, one of $R^3$ and $R^4$ represents hydrogen and the other one is alkyl, $R^5$ represents halo, particularly fluoro, $R^5$ is located at both the ortho-positions with respect to the Y group (that is, both the meta-positions with respect to the X group), and n is 2.

In still another embodiment, as a combination of respective substituents in the compound represented by Formula (I), a combination is preferable in which A represents $SO_2$, Z represents CO, X represents S, Y represents O, $R^2$ represents alkyl, $R^1$ represents hydrogen, alkyl, or halo, and in a case where $R^1$ represents alkyl or halo, $R^1$ is located at the para-position, both of $R^3$ and $R^4$ represent hydrogen, each $R^5$ independently represents alkyl, alkenyl, alkynyl, or halo, and n represents an integer of 0 to 4.

In an embodiment, from the compound represented by Formula (I), 2-[2,6-difluoro-4-({2-[(phenylsulfonyl)amino]ethyl}thio)phenoxy]acetamide (PEPA), 4-[2-(4-chlorophenylsulfonylamino)ethylthio]-2,6-difluorophenoxyacetamide, N,N-dimethyl-4-[2-(4-chlorophenylsulfonylamino)ethylthio]-2,6-difluorophenoxyacetamide, 4-[2-(4-chlorophenylsulfonylamino)ethylthio]-2-fluorophenoxyacetamide, N,N-dimethyl-4-[2-(4-chlorophenylsulfonylamino)ethylthio]-2-fluorophenoxyacetamide, N,N-dimethyl-4-[2-(phenylsulfonylamino)ethylthio]-2,6-difluorophenoxyacetamide, 4-[2-(phenylsulfonylamino)ethylthio]-2-fluorophenoxyacetamide, and N,N-dimethyl-4-[2-(phenylsulfonylamino)ethylthio]-2-fluorophenoxyacetamide, which do not contain a radioisotope, are excluded.

Specific examples of the compound represented by Formula (I) include the following compounds:

TABLE 1

| | Compound name | Abbreviation | Structural formula |
|---|---|---|---|
| 1 | [4-[2-(Benzenesulfonyl-Methyl-Amino)-Ethylsulfanil-2,6-Difluoro-Phenoxy]-Acetamide | K-2 | |

TABLE 1-continued

| | Compound name | Abbreviation | Structural formula |
|---|---|---|---|
| 2 | 2-[4-(2-Benzenesulfonylamino-Ethylsulfanil)-2,6-Difluoro-Phenoxy]-N-Methyl-Acetamide | M-1 | |
| 3 | 2-{2,6-Difluoro-4-[2-(4-Fluoro-Benzenesulfonylamino)-Ethylsulfanil]-Phenoxy}-Acetamide | M-2 | |
| 4 | 2-{2,6-Difluoro-4-[2-(4-Methyl-Benzenesulfonylamino)-Ethylsulfanil]-Phenoxy}-Acetamide | M-3 | |

In an embodiment, in the compound represented by Formula (I), or the pharmaceutically acceptable salt or solvate thereof, one or more atoms constituting the compound are a radioisotope of the atom or atoms, that is, the compound represented by Formula (I), or the pharmaceutically acceptable salt or solvate thereof is a compound represented by the following Formula (I), or a pharmaceutically acceptable salt or solvate:

[Chem. 3]

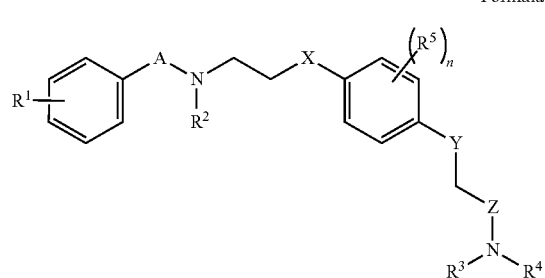

Formula (I)

(in the formula,
each of A and Z independently represents CO, SO, or $SO_2$;
each of X and Y independently represents S or O;
each of $R^1$ to $R^4$ independently represents hydrogen, alkyl, alkenyl, alkynyl, or halo;
each $R^5$ independently represents alkyl, alkenyl, alkynyl, or halo;
n represents an integer of 0 to 4; and
one or more atoms are a radioisotope of the atom or atoms.)

In the compound represented by Formula (I), the radioisotope is selected from the group consisting of $^{15}O$, $^{13}N$, $^{11}C$, $^{18}F$, and the like, but is not particularly limited. From the viewpoint of half-life, the radioisotope is preferably $^{11}C$ or $^{18}F$.

Preferably, one, two, three, or four, preferably, one of $R^1$ to $R^4$ is a group containing a radioisotope (for example, [$^{11}C$]alkyl (preferably, $^{11}CH_3$), [$^{11}C$]alkenyl or [$^{11}C$]alkynyl, or $^{13}F$).

As for the compound represented by Formula (I), preferably, A represents $SO_2$, Z represents CO, X represents S, Y represents O, $R^2$ represents alkyl, $R^1$ represents hydrogen, alkyl, or halo, and in a case where $R^1$ represents alkyl or halo, $R^1$ is located at the para-position, one of $R^3$ and $R^4$ represents hydrogen and the other one is alkyl, $R^5$ represents halo, particularly fluoro, $R^5$ is located at both the ortho-positions with respect to the Y group (that is, both the meta-positions with respect to the X group), n is 2, one of R1 to R4 is a group containing a radioisotope (for example,

[$^{11}$C]alkyl (preferably, $^{11}$CH$_3$), [$^{11}$C]alkenyl or [$^{11}$C]alkynyl, or $^{13}$F). In still another embodiment, as for the compound represented by Formula (I), more preferably, A represents SO$_2$, Z represents CO, X represents S, Y represents O, R$^2$ represents alkyl, R$^1$ represents hydrogen, alkyl, or halo, and in a case where R$^1$ represents alkyl or halo, R$^1$ is located at the para-position, one of R$^3$ and R$^4$ represents hydrogen and the other one is alkyl, R$^5$ represents halo, particularly fluoro, R$^5$ is located at both the ortho-positions with respect to the Y group (that is, both the meta-positions with respect to the X group), n is 2, one of R$^1$ to R$^4$ is a group containing a radioisotope (for example, [$^{11}$C]alkyl (preferably $^{11}$CH$_3$), [$^{11}$C]alkenyl or [$^{11}$C]alkynyl, or $^{18}$F).

Specific examples of the compound containing a radioisotope include the following compounds:

3. Producing Method and Intermediate

Synthesis Example 1

The compound represented by Formula (I), or the pharmaceutically acceptable salt or solvate thereof, in which R$^2$ represents alkyl, alkenyl, or alkynyl can be produced, for example, by reacting a compound represented by the following Formula (II), or a pharmaceutically acceptable salt or solvate thereof (in the formula, A, X, Y, Z, R$^1$, R$^3$, R$^4$, R$^5$, and n are the same as defined in the compound represented by Formula (I)) with X$^1$—R$^2$ (in the formula, R$^2$ represents alkyl, alkenyl, or alkynyl and X$^1$ represents halogen):

TABLE 2

| | Compound name | Abbreviation | Structural formula |
|---|---|---|---|
| 1' | {4-[2-(Benzenesulfonyl-[$^{11}$C]Methyl-Amino)-Ethylsulfanil]-2,6-Difluoro-Phenoxy}-Acetamide | Radio-labeled K-2 | |
| 2' | 2-[4-(2-Benzenesulfonylamino-Ethylsulfanil)-2,6-Difluoro-Phenoxy]-N-[$^{11}$C]Methyl-Acetamide | Radio-labeled M-1 | |
| 3' | 2-{2,6-Difluoro-4-[2-(4-[$^{18}$F]Fluoro-Benzenesulfonylamino)-Ethylsulfanil]-Phenoxy}-Acetamide | Radio-labeled M-2 | |
| 4' | 2-{2,6-Difluoro-4-[2-(4-[$^{11}$C]Methyl-Benzenesulfonylamino)-Ethylsulfanil]-Phenoxy}-Acetamide | Radio-labeled M-3 | |

[Chem. 4]

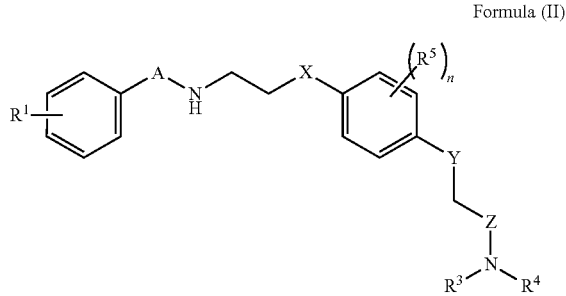

Formula (II)

In an embodiment, both the $R^3$ and the $R^4$ in Formula (I) and Formula (II) represent hydrogen. In an embodiment, $R^2$ represents [$^{11}$C]alkyl, [$^{11}$C]alkenyl, or [$^{11}$C]alkynyl, and $R^2$ preferably represents [$^{11}$C]alkyl, particularly $^{11}$CH$_3$. In an embodiment, $X^1$ represents I. As a specific examples of the compound represented by Formula (II), 2-[2,6-difluoro-4-({2-[(phenylsulfonyl)amino]ethyl}thio)phenoxy]acetamide (PEPA) is exemplified.

The reaction can be performed in a polar aprotic solvent such as dimethylformamide (DMF), tetrahydrofuran, acetonitrile, acetone, or dimethylsulfoxide. Further, the reaction is preferably performed using a base such as NaOH under a basic condition. The reaction temperature is room temperature to reflux temperature, and particularly, is preferably 60 to 100° C. and more preferably 80° C. The reaction time is 1 minute to 10 minutes, and particularly 5 minutes.

The PET probe has to be produced in a short time and with a high yield since the radioisotope usually has a short half-life. The reaction is suitable for the production of the PET probe since the reaction quantitatively progresses in a short time.

The present inventors have found that the reaction of the compound represented by Formula (II) with $X^1$—$R^2$ quantitatively occurs in a NH group adjacent to the A group of the compound represented by Formula (II). Therefore, even if $R^3$ and $R^4$ represent hydrogen, only the NH group can be substituted with an N—$R^2$ group without use of a protecting group.

The compound represented by Formula (II), or the pharmaceutically acceptable salt or solvate thereof can be used as an intermediate used for producing the compound represented by Formula (I), or the pharmaceutically acceptable salt or solvate thereof, in which $R^2$ represents alkyl, alkenyl, or alkynyl. Further, the compound represented by Formula (II), or the pharmaceutically acceptable salt or solvate thereof can be used as an intermediate used for producing the radio-labeled compound represented by Formula (I), or the pharmaceutically acceptable salt or solvate thereof, in which $R^2$ represents [$^{11}$C]alkyl, [$^{11}$C]alkenyl, or [$^{11}$C]alkynyl.

Synthesis Example 2

The compound represented by Formula (I), or the pharmaceutically acceptable salt or solvate thereof, in which $R^1$ represents alkyl, alkenyl, or alkynyl can be produced, for example, by reacting a compound represented by the following Formula (III), or pharmaceutically acceptable salt or solvate

[Chem. 5]

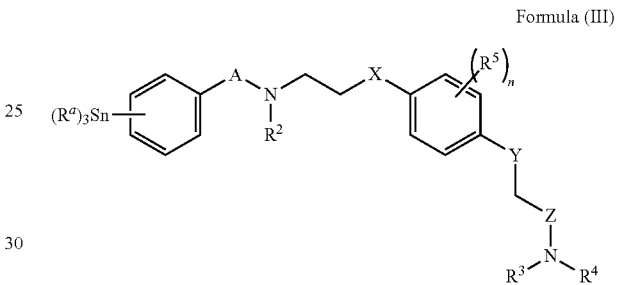

Formula (III)

(in the formula, A, X, Y, Z, $R^2$, $R^3$, $R^4$, $R^5$, and n are the same as defined above and each $R^a$ independently represents alkyl, alkenyl, or alkynyl) with $X^1$—$R^1$ (in the formula, $R^1$ is the same as defined above and $X^1$ represents halogen). In an embodiment, all $R^a$'s are n-butyl. In an embodiment, $R^1$ represents [$^{11}$C]alkyl, [$^{11}$C]alkenyl, or [$^{11}$C]alkynyl, and $R^1$ preferably represents [$^{11}$C]alkyl, particularly $^{11}$CH$_3$. In an embodiment, $X^1$ represents I.

Specific examples of the compound represented by Formula (III) include the following:

TABLE 3

| | Compound name | Abbreviation | Structural formula |
|---|---|---|---|
| 5 | 2-(2,6-Difluoro-4-((2-(4-(Tributylstannyl)Phenylsulfonamide)Ethyl)Thio)Phenoxy)Acetamide | M-3pre | (structure shown) |

The reaction can be performed in the presence of a palladium catalyst, a phosphine ligand, a carbonate, and a copper halide. The palladium catalyst is, for example, tris (dibenzylideneacetone)dipalladium or the like. Further, the phosphine ligand is, for example, tri(o-tolyl)phosphine, (ditert-butyl)methylphosphine, or the like. The carbonate is $K_2CO_3$ or the like. The copper halide is CuCl or the like. The reaction can be performed in a polar aprotic solvent such as dimethylformamide (DMF), tetrahydrofuran, acetonitrile, acetone, or dimethylsulfoxide. The reaction temperature is room temperature to reflux temperature, and particularly, is preferably 60 to 100° C. and more preferably 80° C. The reaction time is 1 minute to 10 minutes, and particularly 5 minutes.

The PET probe has to be produced in a short time and with a high yield since the radioisotope usually has a short half-life. The reaction is suitable for the production of the PET probe since the reaction quantitatively progresses in a short time.

The compound represented by Formula (III), or the pharmaceutically acceptable salt or solvate thereof can be used as an intermediate used for producing the compound represented by Formula (I), or the pharmaceutically acceptable salt or solvate thereof, in which $R^1$ represents alkyl, alkenyl, or alkynyl. Further, the compound represented by Formula (III), or the pharmaceutically acceptable salt or solvate thereof can be used as an intermediate used for producing the radio-labeled compound represented by Formula (I), or the pharmaceutically acceptable salt or solvate thereof, in which $R^1$ represents [$^{11}$C]alkyl, [$^{11}$C]alkenyl, or [$^{11}$C]alkynyl.

The compound represented by Formula (I), or the pharmaceutically acceptable salt or solvate thereof can be produced by the method described in the following Examples.

4. Use

The compound represented by Formula (I), or the pharmaceutically acceptable salt or solvate thereof can specifically bind to an AMPA receptor. Therefore, the compound represented by Formula (I), or the pharmaceutically acceptable salt or solvate thereof can be used for imaging an AMPA receptor. In particular, the compound can be used as a molecular probe, for example, a PET probe.

The imaging includes molecular imaging, for example, positron emission tomography (PET), a multi-photon imaging method, a two-photon imaging method, a near-infrared fluorescence imaging method, autoradiography, single photon emission computed tomography (SPECT), and the like. The imaging is preferably PET imaging.

The present invention provides a composition for imaging an AMPA receptor, the composition containing a compound represented by Formula (I), or a pharmaceutically acceptable salt or solvate thereof. The composition can contain a pharmaceutically acceptable carrier. The pharmaceutically acceptable carrier is not particularly limited, and examples thereof include sterilized water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

The contents of the compound represented by Formula (I), or the pharmaceutically acceptable salt or solvate thereof and the pharmaceutically acceptable carrier in the composition are not particularly limited, and these are determined based on various factors such as: the type of the compound that is used; the age, weight, health conditions, sex, and content of diet of the mammals that receive an administration; the number of administration and the route of administration; the period of treatment; and other medicines that are used at the same time. The content of the compound represented by Formula (I), or the pharmaceutically acceptable salt or solvate thereof is not particularly limited as long as it is such an amount that the AMPA receptor can be imaged. The composition is preferably produced such that the compound represented by Formula (I), or the pharmaceutically acceptable salt or solvate thereof can be administered. The content of the pharmaceutically acceptable carrier can be set, for example, to an amount of 1 to 99% by weight of the composition.

Further, the present invention provides a compound represented by Formula (I) being used for imaging an AMPA receptor, or a pharmaceutically acceptable salt or solvate thereof. Furthermore, the present invention provides use of a compound represented by Formula (I), or a pharmaceutically acceptable salt or solvate thereof in production of a pharmacological agent used for imaging an AMPA receptor.

Further, the present invention provides a method for imaging an AMPA receptor, the method including administering an effective dose of a compound represented by Formula (I), or a pharmaceutically acceptable salt or solvate thereof, to a mammal. The mammal includes, for example, a rat, a mouse, a guinea pig, a hamster, and the like. The method of administration is not particularly limited, and for example, parenteral administration, intravenous administration, or intraperitoneal administration may be used. Preferably, intravenous administration may be used. The amount of administration is not particularly limited as long as it is such an amount that the AMPA receptor can be imaged.

Further, the present invention provides a kit used for imaging an AMPA receptor, the kit containing a compound represented by Formula (I), or a pharmaceutically acceptable salt or solvate thereof. Furthermore, the present invention provides an intermediate used for producing a compound represented by Formula (I), or a pharmaceutically acceptable salt or solvate thereof, for example, a kit used for imaging an AMPA receptor, the kit containing a compound represented by Formula (II), or a pharmaceutically acceptable salt or solvate thereof; and/or a compound represented by Formula (III), or a pharmaceutically acceptable salt or solvate thereof. The kit can be further contain an instruction to instruct an amount of administration, administration method, use method, and storage method for the compound, and/or a method for imaging an AMPA receptor. The kit can be further contain a reagent for radioactive labeling, for example, halogenated [$^{11}$C]alkyl, halogenated [$^{11}$C]alkenyl, halogenated [$^{11}$C]alkynyl, or the like. Furthermore, the present invention provides a method for imaging an AMPA receptor, the method including a step of detecting radiation emitted from the brain of a subject to which a compound represented by Formula (I), or a pharmaceutically acceptable salt or solvate thereof has been administered.

EXAMPLES

5 Examples

Examples will be described below. The following Examples will be described only to deepen the understanding of the claims of the present invention, and are by no means intended to limit the claims of the present invention.

Example 1

Synthesis of K-1 and K-2

2-[2,6-Difluoro-4-({2-[(phenylsulfonyl)amino]ethyl}thio)phenoxy]acetamide (K-1, PEPA) and {4-[2-(benzenesulfonyl-methyl-amino)-ethylsulfanil]-2,6-difluoro-phenoxy}-acetamide (K-2) were synthesized by the following scheme. The $^1$H NMR spectrum of each compound was recorded with Bruker Avance III 400 MHz or Varian Mercury plus-300 MHz by using TMS as an internal reference.

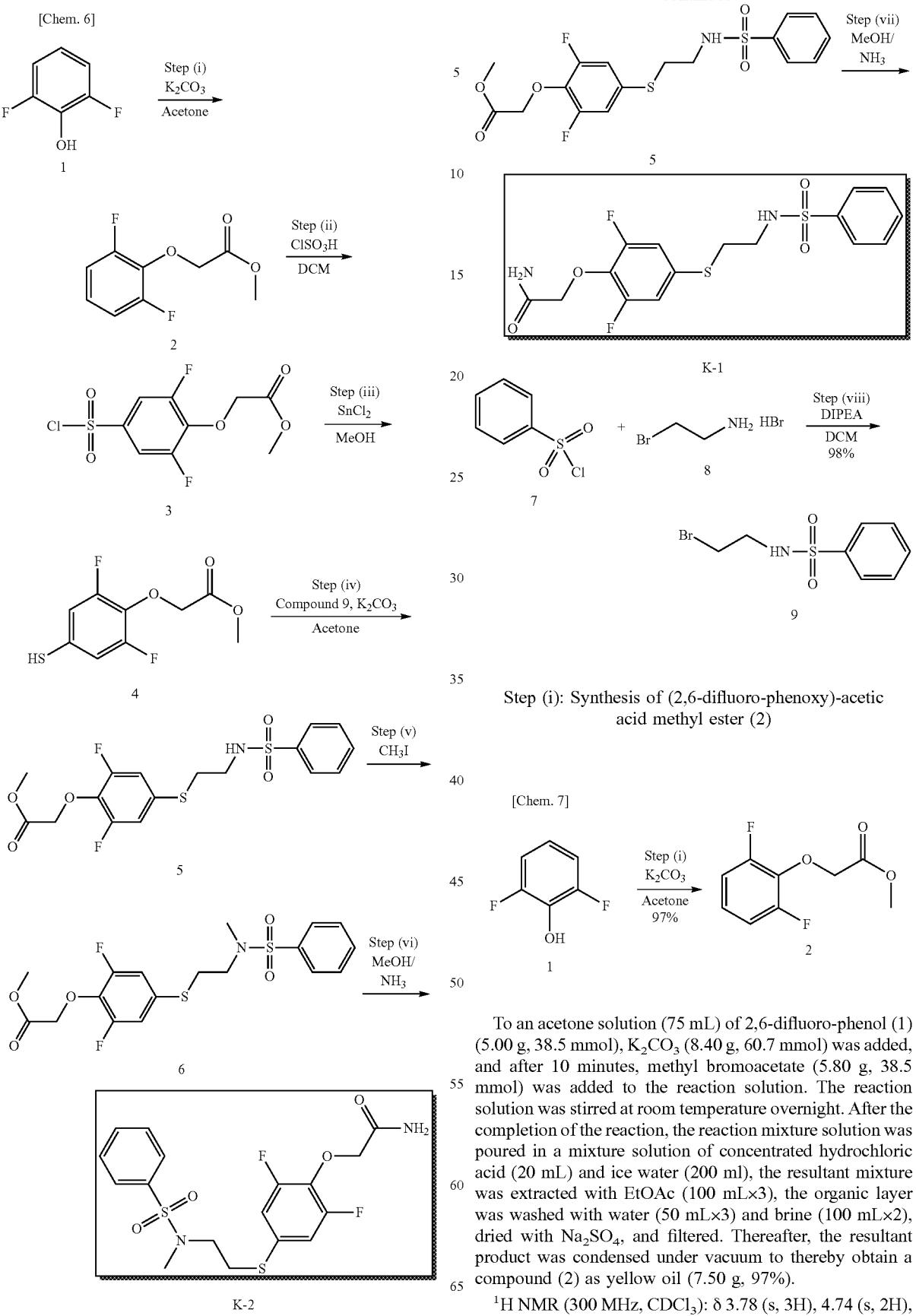

Step (i): Synthesis of (2,6-difluoro-phenoxy)-acetic acid methyl ester (2)

To an acetone solution (75 mL) of 2,6-difluoro-phenol (1) (5.00 g, 38.5 mmol), $K_2CO_3$ (8.40 g, 60.7 mmol) was added, and after 10 minutes, methyl bromoacetate (5.80 g, 38.5 mmol) was added to the reaction solution. The reaction solution was stirred at room temperature overnight. After the completion of the reaction, the reaction mixture solution was poured in a mixture solution of concentrated hydrochloric acid (20 mL) and ice water (200 ml), the resultant mixture was extracted with EtOAc (100 mL×3), the organic layer was washed with water (50 mL×3) and brine (100 mL×2), dried with $Na_2SO_4$, and filtered. Thereafter, the resultant product was condensed under vacuum to thereby obtain a compound (2) as yellow oil (7.50 g, 97%).

$^1$H NMR (300 MHz, $CDCl_3$): δ 3.78 (s, 3H), 4.74 (s, 2H), 6.86-6.99 (m, 3H).

Step (ii): Synthesis of (4-chlorosulfonyl-2,6-difluoro-phenoxy)-acetic acid methyl ester (3)

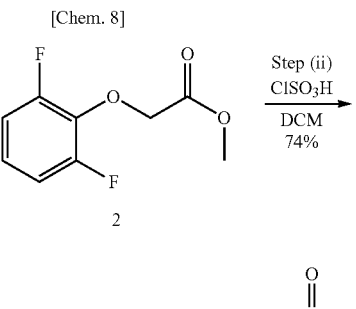

To a DCM solution of (2,6-difluoro-phenoxy)-acetic acid methyl ester (2) (5.00 g, 24.7 mmol), chlorosulfonic acid (17.2 g, 24.7 mmol) was added dropwise in an ice bath, and the reaction solution was heated to 45° C. and stirred for 1.5 hours. After the completion of the reaction, the reaction mixture solution was quenched with 50 mL of ice water, the organic layer was separated and washed with water (300 mL×3). The resultant product was dried with $Na_2SO_4$ and filtered, and then was condensed under vacuum, thereby obtaining a compound (3) as yellow oil (5.50 g, 74%).

$^1$H NMR (300 MHz, $CDCl_3$): δ 3.81 (s, 3H), 4.96 (s, 2H), 7.61 (s, 1H), 7.64 (s, 1H).

Step (iii): Synthesis of (2,6-difluoro-4-mercapto-phenoxy)-acetic acid methyl ester (4)

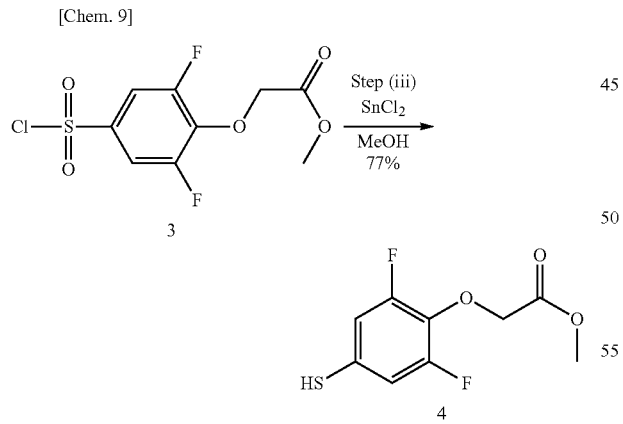

To a mixture solution of (4-chlorosulfonyl-2,6-difluoro-phenoxy)-acetic acid methyl ester (3) (5.50 g, 18.3 mmol), $SnCl_2$ (14.5 g, 64.2 mmol), and methanol (50 mL), concentrated hydrochloric acid (25 mL) was added dropwise. The reaction mixture solution was heated to reflux temperature and stirred for 2 hours. After cooling, the reaction mixture solution was poured to ice water (100 mL) and the resultant mixture was extracted with DCM (100 mL×3). The organic layer was washed with water (100 mL×3) and brine (100 mL×2), dried with $Na_2SO_4$, filtered, and then condensed under vacuum, thereby obtaining a compound (4) as yellow oil (3.30 g, 77%).

$^1$H NMR (300 MHz, $CDCl_3$): δ 3.52 (s, 1H), 3.77 (s, 3H), 4.71 (s, 2H), 6.83 (s, 1H), 6.86 (s, 1H).

Step (iv): Synthesis of [4-(2-benzenesulfonylamino-ethylsulfanil)-2,6-difluoro-phenoxy]-acetic acid methyl ester (5)

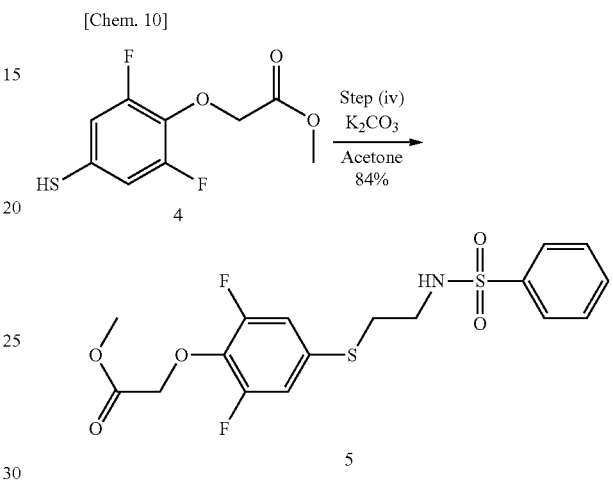

A mixture solution of (2,6-difluoro-4-mercapto-phenoxy)-acetic acid methyl ester (4) (1.10 g, 4.7 mmol), potassium carbonate (778 mg, 5.6 mmol), and acetone (15 mL) was stirred under $N_2$ at room temperature for 20 minutes. To the reaction solution, N-(2-bromo-ethyl)-benzenesulfonamide (9) (1.30 g, 4.90 mmol) was added, and the reaction solution was stirred at room temperature overnight. After the completion of the reaction, the reaction solution was poured to 30 mL of 2N HCl and the resultant product was extracted with EtOAc (50 mL×3). The organic layer was washed with water (50 mL×3) and brine (100 mL×2), dried with $Na_2SO_4$, filtered, and then condensed under vacuum, thereby obtaining a residue. The residue was refined by silica gel column chromatography (PE/EA=10/1 to 3/1, v/v) to thereby obtain a compound (5) as yellow oil (1.60 g, 84%). $^1$HNMR (300 MHz, $CDCl_3$): δ 2.95 (t, J=6.6 Hz, 2H), 3.12 (q, J=6.3 Hz, 2H), 3.78 (s, 3H), 4.72 (s, 2H), 5.20 (t, J=6.0 Hz, 1H), 6.76-6.83 (m, 2H), 7.47-7.60 (m, 3H), 7.82-7.84 (m, 2H).

Step (v): Synthesis of {4-[2-(benzenesulfonyl-methyl-amino)-ethylsulfanil]-2,6-difluoro-phenoxy}-acetic acid methyl ester (6)

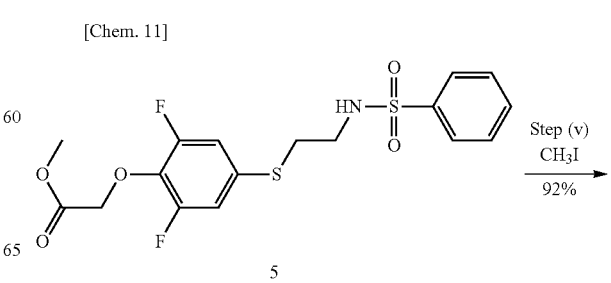

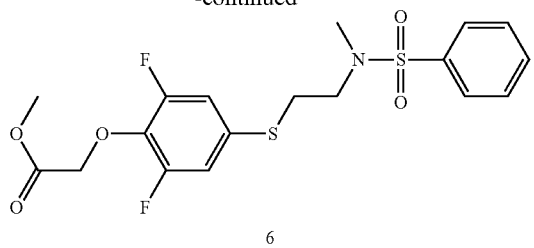

6

To 10 mL of a DMF mixture solution of [4-(2-benzenesulfonylamino-ethylsulfanil)-2,6-difluoro-phenoxy]-acetic acid methyl ester (5) (300 mg, 0.72 mmol) and K$_2$CO$_3$ (397 mg, 2.88 mmol), MeI (255 mg, 1.80 mmol) was added at 0° C. Thereafter, the reaction solution was stirred at room temperature for 1 hour. After the completion of the reaction, the reaction solution was diluted with 20 ml of water and extracted with EtOAc (30 mL×3). The organic layer was washed with water (30 mL×3) and brine (20 mL×2), dried with Na$_2$SO$_4$, filtered, and then condensed under vacuum, thereby obtaining a compound (6) as yellow oil (285 mg, 92%).

$^1$HNMR (300 MHz, CDCl$_3$): δ 2.81 (s, 3H), 3.04-3.09 (m, 2H), 3.19-3.24 (m, 2H), 3.79 (s, 3H), 4.74 (s, 2H), 6.90-6.94 (m, 2H), 7.50-7.60 (m, 3H), 7.74-7.77 (m, 2H).

Step (vi): Synthesis of {4-[2-(benzenesulfonyl-methyl-amino)-ethylsulfanil]-2,6-difluoro-phenoxy}-acetamide (K-2)

[Chem. 12]

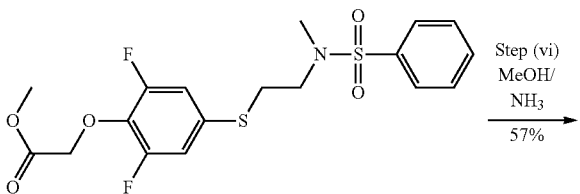

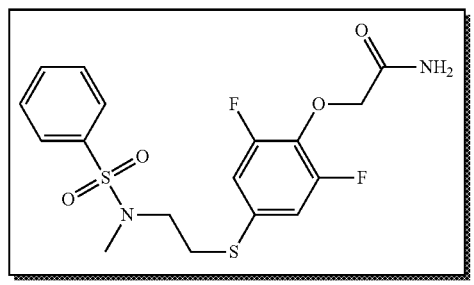

K-2

A mixture solution of {4-[2-(benzenesulfonyl-methyl-amino)-ethylsulfanil]-2,6-difluoro-phenoxy}-acetic acid methyl ester (6) (40.0 mg, 0.09 mmol) and 13 mL of 4N MeOH/NH$_3$ was stirred at room temperature for 18 hours. After the completion of the reaction, the reaction mixture solution was condensed under vacuum, thereby obtaining a residue. The residue was refined by preparative HPLC to thereby obtain compound (K-2) as a white solid (22.0 mg, 57%).

$^1$HNMR (300 MHz, CDCl$_3$): δ 2.82 (s, 3H), 3.08-3.13 (m, 2H), 3.20-3.26 (m, 2H), 4.58 (s, 2H), 6.93-6.99 (m, 2H), 7.50-7.63 (m, 3H), 7.75-7.78 (m, 2H).

Step (vii): Synthesis of 2-[2,6-difluoro-4-({2-[(phenylsulfonyl)amino]ethyl}thio)phenoxy]acetamide (K-1)

[Chem. 13]

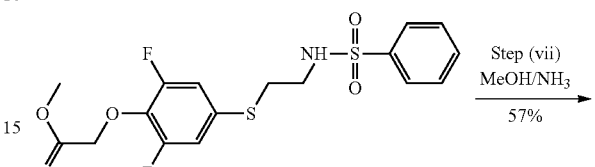

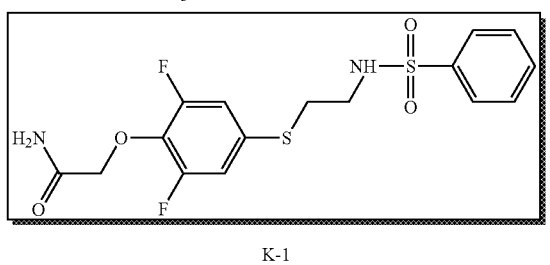

K-1

A mixture solution of [4-(2-benzenesulfonylamino-ethylsulfanil)-2,6-difluoro-phenoxy]-acetic acid methyl ester (5) (200 mg, 0.48 mmol) and 10 mL of 4N MeOH/NH$_3$ was stirred at room temperature for 18 hours. After the completion of the reaction, the reaction mixture solution was condensed under vacuum, thereby obtaining a residue. The residue was refined by preparative HPLC to thereby obtain a compound K-1 as a white solid (110 mg, 57%).

$^1$HNMR (300 MHz, CDCl$_3$+D$_2$O): δ 2.97-3.02 (m, 2H), 3.11-3.16 (m, 2H), 4.56 (s, 2H), 6.82-6.90 (m, 2H), 7.48-7.61 (m, 3H), 7.82-7.87 (m, 2H).

Step (viii): Synthesis of N-(2-bromo-ethyl)-benzenesulfonamide (9)

[Chem. 14]

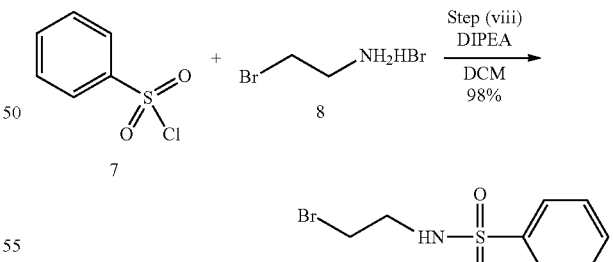

To a DCM (30 mL) solution of benzenesulfonyl chloride (7) (3.00 g, 17.0 mmol) and 2-bromoethylamine hydrobromide (8) (3.80 g, 18.7 mmol), DIPEA (4.80 g, 37.4 mmol) was added in an ice bath. Thereafter, the reaction solution was stirred at the same temperature for 1.5 hours. After the completion of the reaction, the reaction solution was diluted with 20 mL of water and extracted with EtOAc (30 mL×3). The organic layer was washed with water (30 mL×3) and brine (20 mL×2), dried with Na$_2$SO$_4$, filtered, and then condensed under vacuum, thereby obtaining a compound (9) as a white solid (4.40 g, 98%). $^1$HNMR (300 MHz, CDCl$_3$): δ 3.36-3.39 (m, 4H), 5.09 (s, 1H), 7.50-7.63 (s, 3H), 7.87-7.89 (s, 2H).

Example 2

Synthesis of M-1, M-2, and M-3

According to the following scheme, 2-[4-(2-benzenesulfonylamino-ethylsulfanil)-2,6-difluoro-phenoxy]-N-methyl-acetamide (M-1), 2-{2,6-difluoro-4-[2-(4-fluoro-benzenesulfonylamino)-ethylsulfanil]-phenoxy}-acetamide (M-2), and 2-{2,6-difluoro-4-[2-(4-methyl-benzenesulfonylamino)-ethylsulfanil]-phenoxy}-acetamide (M-3) were synthesized. The $^1$H NMR spectrum of each compound was recorded with Varian Mercury plus-400 MHz by using TMS as an internal reference. The following one was used as LCMS: Agilent 1200A, column: C18; column size: 4.6*50 minutes; mobile phase: B (ACN), A (water of 0.05% NH$_3$); gradient (B %): as described in Example).

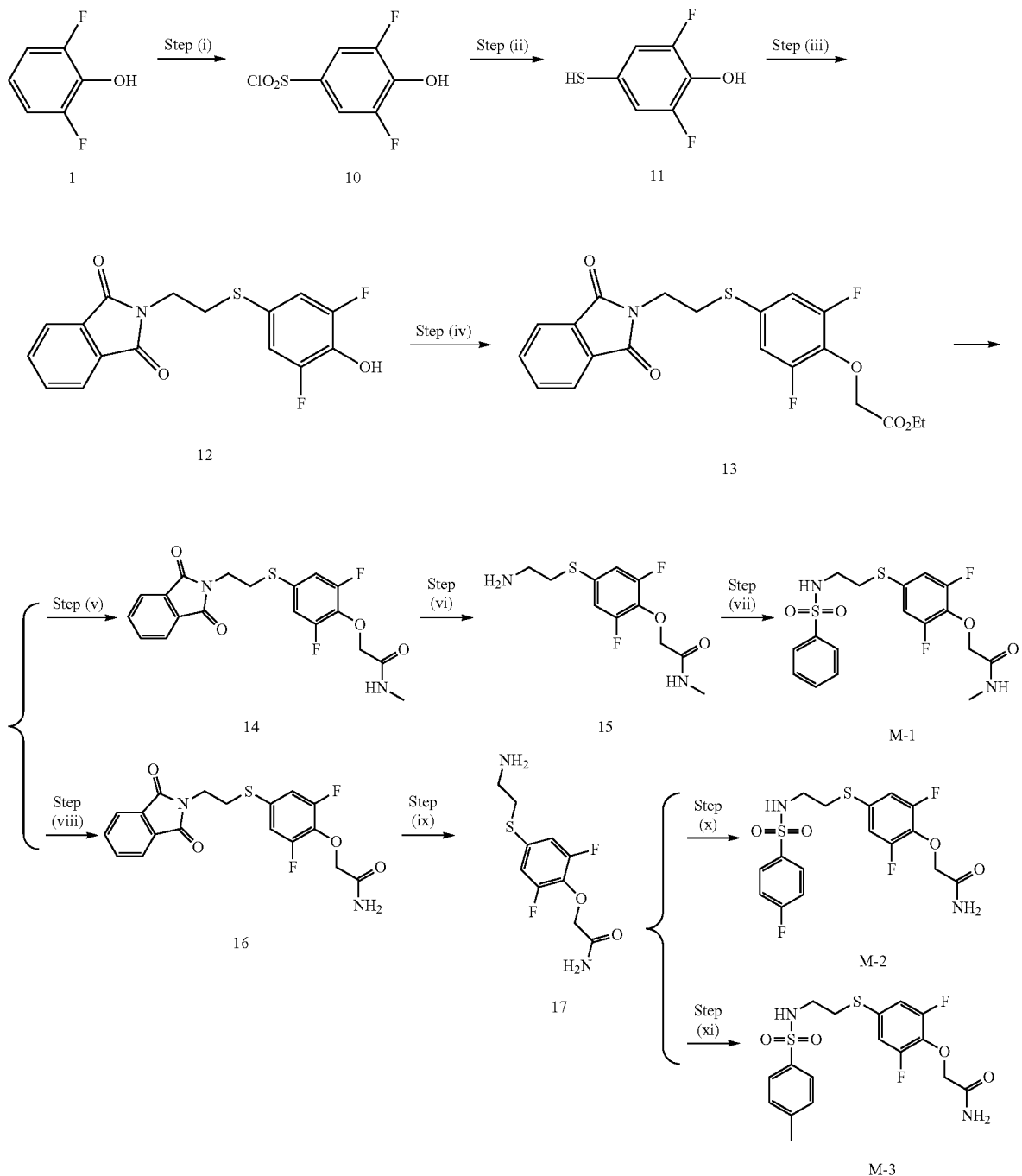

Step (i): Synthesis of 3,5-difluoro-4-hydroxy-benzenesulfonyl chloride (10)

[Chem. 16]

To a DCM (50 mL) solution of the compound (1) (5.0 g), chlorosulfonic acid (15 mL) was added dropwise. The reaction mixture solution was stirred at 25° C. for 1 hour. The TLC (petroleum ether/EtOAc: 20/1) indicated the completion of the reaction. Thereafter, the solution was poured to crushed ice. The organic layer was separated and filtered through Celite. The filtrate was dried and distilled under vacuum to thereby obtain a compound (10) as yellow oil: 5 g (57%).

$^1$H-NMR (400 MHz, CDCl$_3$): δ 6.30 (s, 1H), 7.66-7.68 (m, 2H).

Step (ii): Synthesis of 2,6-difluoro-4-mercapto-phenol (11)

[Chem. 17]

To a DCM (3 mL) solution of triphenyl phosphine (3.4 g, 13.1 mmol) and DMF (0.1 mL), a DCM (4 mL) solution of the compound (10) (1.0 g, 4.3 mmol) was added dropwise at 0° C. under nitrogen. The reaction mixture solution was stirred at 25° C. for 2 hours. Thereafter, 1N HCl was added to the mixture solution to adjust pH to 3 and the mixture solution was extracted with EA. The organic layer was dried with sodium sulfate to remove the solvent, thereby obtaining a crude compound (11) as yellow oil.

Step (iii): Synthesis of 2-[2-(3,5-difluoro-4-hydroxy-phenylsulfanyl)-ethyl]-isoindole-1,3-dione (12)

[Chem. 18]

To a DMF (100 mL) solution of the crude compound (11) (14 g, 86 mmol), 2-(2-bromo-ethyl)-isoindole-1,3-dione (13.2 g, 51.8 mmol) and K$_2$CO$_3$ (23.8 g, 172.4 mmol) were added. The mixture solution was stirred at 25° C. overnight. Thereafter, 1N HCl was added to the mixture solution to adjust pH to 3 and the mixture solution was extracted with EA. The organic layer was dried with sodium sulfate to remove the solvent, thereby obtaining a compound (12) as a yellow solid (8 g, 27%).

$^1$H-NMR (400 MHz, DMSO_d6): δ 3.20-3.23 (t, 2H), 3.75-3.79 (t, 2H), 7.08-7.10 (d, 2H), 7.84 (s, 4H).

Step (iv): Synthesis of {4-[2-(1,3-dioxo-1,3-dihydro-isoindole-2-yl)-ethylsulfanil]-2,6-difluoro-phenoxy}-ethyl acetic acid ester (13)

[Chem. 19]

To a solution obtained by dissolving the compound (12) (5.0 g, 15 mmol) in DMF (30 mL), 3-bromo-propionic acid ethyl ester (2.5 g, 15 mmol) and K$_2$CO$_3$ (3.0 g, 22.5 mmol) were added. The mixture solution was stirred at 25° C. overnight. Thereafter, the mixture solution was extracted with EA. The organic layer was dried with sodium sulfate to remove the solvent, thereby obtaining a compound (13) as a white solid (6 g, 97%).

$^1$H-NMR (400 MHz, CDCl$_3$): δ 1.21-1.24 (t, 3H), 3.11-3.14 (t, 2H), 3.84-3.88 (t, 2H), 4.18-4.20 (d, 2H), 4.61 (s, 2H), 6.91-6.94 (d, 2H), 7.66-7.68 (m, 2H), 7.77-7.79 (m, 2H).

Step (v): Synthesis of 2-{4-[2-(1,3-dioxo-1,3-dihydro-isoindole-2-yl)-ethylsulfanil]-2,6-difluoro-phenoxy}-N-methyl-acetamide (14)

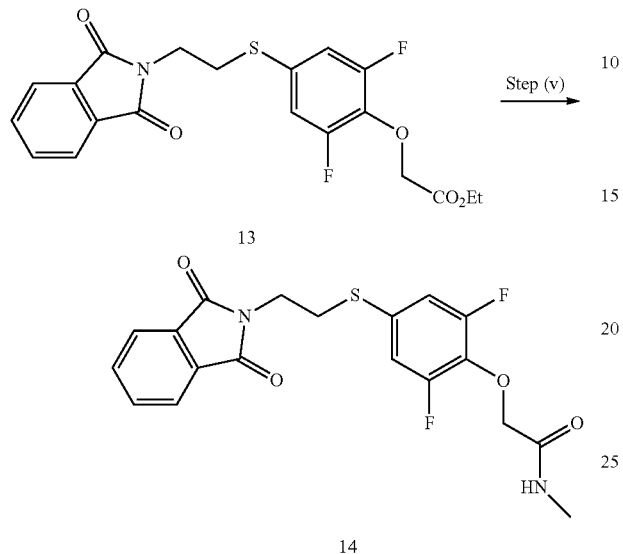

A methylamine alcohol solution (10 mL) of the compound (13) (0.5 g, 1.2 mmol) was stirred at 100° C. for 30 minutes. Thereafter, the mixture solution was condensed to thereby obtain a crude compound (14) as yellow oil (1 g).

Step (vi): Synthesis of 2-[4-(2-amino-ethylsulfanil)-2,6-difluoro-phenoxy]-N-methyl-acetamide (15)

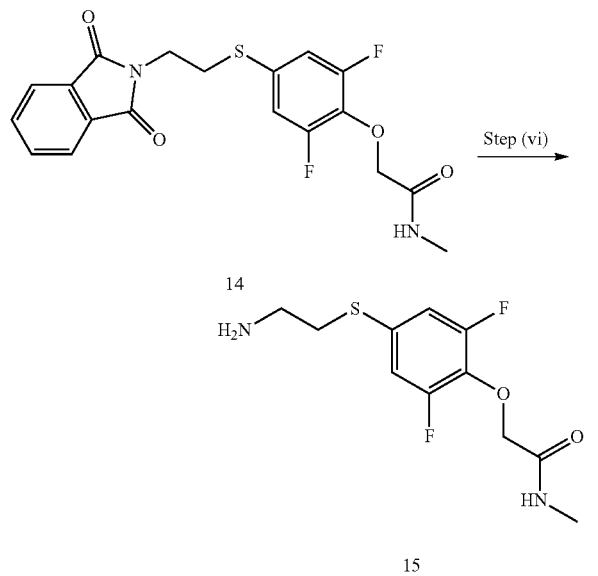

Hydrazine hydrate (0.25 g, 5 mmol) was added to an EtOH (10 mL) solution of the crude compound (14) (1 g, 2.5 mmol) at 90° C. The solution was heated to 90° C., stirred for 30 minutes, and then cooled at room temperature. The resultant product was filtered and washed with EtOH. The organic layer was dried with sodium sulfate and condensed to thereby obtain a crude compound (15) as yellow oil (0.5 g).

Step (vii): Synthesis of 2-[4-(2-benzenesulfonylamino-ethylsulfanil)-2,6-difluoro-phenoxy]-N-methyl-acetamide (M-1)

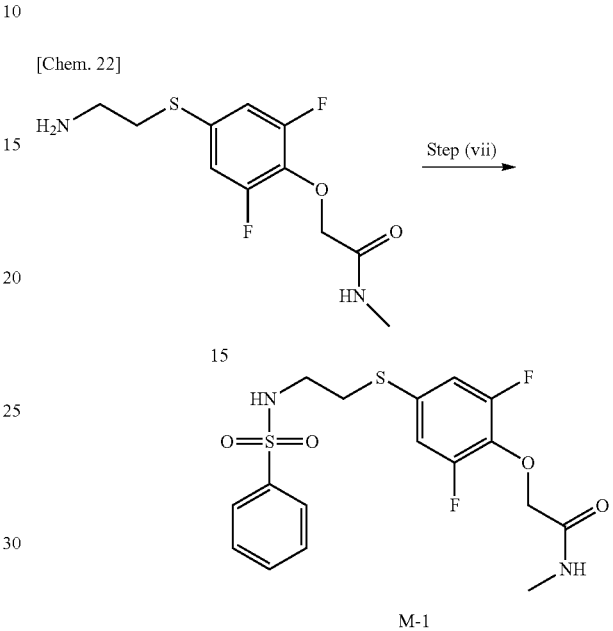

Benzenesulfonyl chloride (0.4 g, 2.2 mmol) and triethylamine (0.2 g, 2.2 mmol) were added to a DCM (10 mL) solution of the crude compound (15) (0.5 g, 1.8 mmol). Thereafter, the mixture solution was stirred at 25° C. for 1 hour and extracted with EA. The organic layer was dried with sodium sulfate and condensed. The residue was refined by flash chromatography to thereby obtain a compound (M-1) as a white solid (20 mg).
$^1$H-NMR (400 MHz, DMSO_d6): δ 2.65-2.66 (d, 3H), 2.91-2.94 (t, 2H), 2.01-3.04 (t, 2H), 4.50 (s, 2H), 7.10-7.12 (d, 2H), 7.57-7.65 (m, 3H), 7.76-7.78 (d, 2H), 7.92-7.95 (t, 1H), 8.05 (s, 1H).
MS: m/z 417 (M+1)$^+$
LCMS [mobile phase: 5% water (0.1% NH$_4$OH) and 95% CH$_3$CN from 90% water (0.1% NH$_4$OH) and 10% CH$_3$CN, 6.0 minutes, finally 0.5 minutes under these conditions] purity 97.4%, Rt=3.341 minutes; MS Calcd.: 416; MS Found: 417 ([M+1]$^+$).

Step (viii): Synthesis of 2-{4-[2-(1,3-dioxo-1,3-dihydro-isoindole-2-yl)-ethylsulfanil]-2,6-difluoro-phenoxy}-acetamide (16)

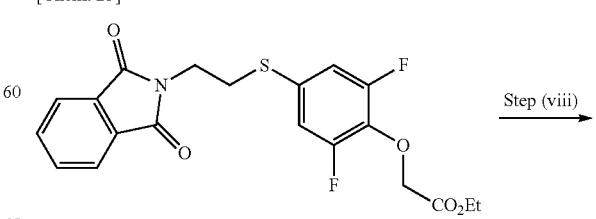

-continued

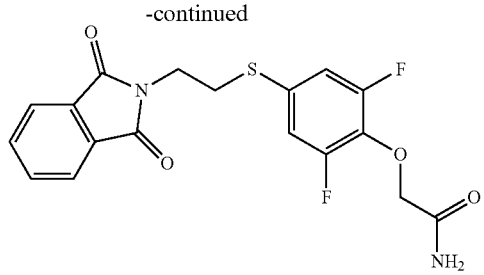

16

An NH₃/EtOH (100 mL) solution of the compound (13) (5.0 g, 11.8 mmol) was stirred at 25° C. for 2 hours. Thereafter, the solution was condensed to thereby obtain a crude compound (16) as yellow oil (6.0 g).

Step (ix): Synthesis of 2-[4-(2-amino-ethylsulfanil)-2,6-difluoro-phenoxy]-acetamide (17)

[Chem. 24]

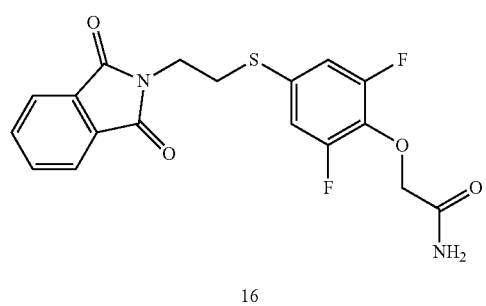

16

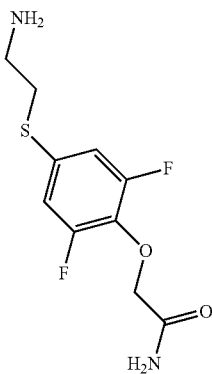

17

Hydrazine hydrate (1.5 g, 30 mmol) was added to an EtOH (50 mL) solution of the crude compound (16) (6.0 g, 15.3 mmol) at 90° C. The solution was heated to 90° C., stirred for 30 minutes, and then cooled at room temperature. The resultant product was filtered and washed with EtOH. The organic layer was dried with sodium sulfate and condensed to thereby obtain a crude compound (17) as yellow oil (4.0 g).

Step (x): Synthesis of 2-{2,6-difluoro-4-[2-(4-fluoro-benzenesulfonylamino)-ethylsulfanil]-phenoxy}-acetamide (M-2)

[Chem. 25]

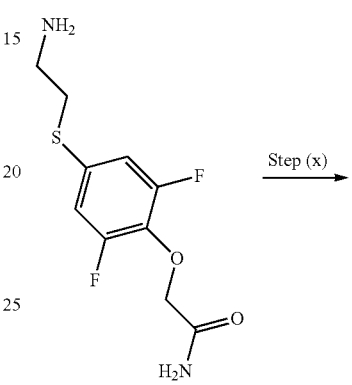

17

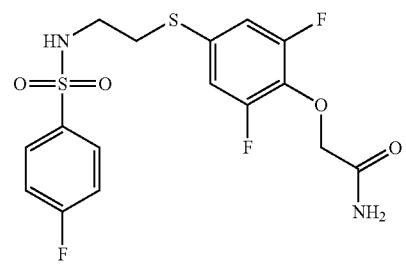

M-2

4-Fluoro-benzenesulfonyl chloride (0.4 g, 2.3 mmol) and triethylamine (0.2 g, 2.2 mmol) were added to a DMF (10 mL) solution of the crude compound 17 (0.5 g, 1.9 mmol). Thereafter, the mixture solution was stirred at 25° C. for 1 hour and extracted with EA. The organic layer was dried with sodium sulfate and condensed. The residue was refined by flash chromatography to thereby obtain a compound (M-2) as a white solid (20 mg).

$^1$H-NMR (400 MHz, DMSO_d6): δ 2.92-2.95 (t, 2H), 3.01-3.04 (t, 2H), 4.45 (s, 2H), 7.09-7.11 (d, 2H), 7.40-7.44 (m, 3H), 7.47 (s, 1H), 7.81-7.85 (m, 2H), 7.95-7.98 (t, 1H).

MS: m/z 421 (M+1)⁺

LCMS [mobile phase: 5% water (0.1% NH₄OH) and 95% CH₃CN from 90% water (0.1% NH₄OH) and 10% CH₃CN, 6 minutes, finally 0.5 minutes under these conditions] purity 95.1%, Rt=3.284 minutes; MS Calcd.: 420; MS Found: 421 ([M+1]⁺).

Step (xi): Synthesis of 2-{2,6-difluoro-4-[2-(4-methyl-benzenesulfonylamino)-ethylsulfanil]-phenoxy}-acetamide (M-3)

[Chem. 26]

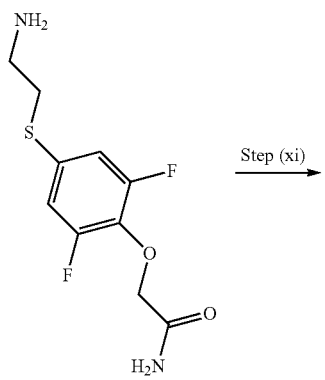

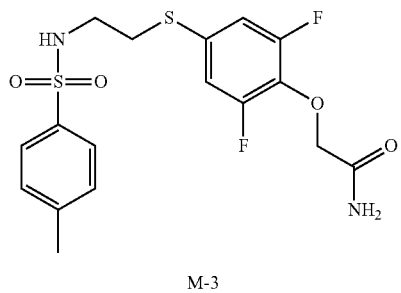

M-3

4-Methyl-benzenesulfonyl chloride (0.5 g, 2.3 mmol) and triethylamine (0.2 g, 2.2 mmol) were added to a DMF (10 mL) of the crude compound (17) (0.5 g, 1.9 mmol). Thereafter, the mixture solution was stirred at 25° C. for 1 hour and extracted with EA. The organic layer was dried with sodium sulfate and condensed. The residue was refined by flash chromatography to thereby obtain a compound (M-3) as a white solid (20 mg).

$^1$H-NMR (400 MHz, DMSO_d6): δ 2.38 (s, 3H), 2.88-2.91 (t, 2H), 2.99-3.02 (t, 2H), 4.49 (s, 2H), 7.08-7.10 (d, 2H), 7.37-7.48 (m, 4H), 7.64-7.66 (d, 2H), 7.81-7.84 (t, 1H).

MS: m/z 417 (M+1)$^+$

LCMS [mobile phase: 5% water (0.1% NH$_4$OH) and 95% CH$_3$CN from 90% water (0.1% NH$_4$OH) and 10% CH$_3$CN, 6.0 minutes, finally 0.5 minutes under these conditions] purity 96.6%, Rt=3.365 minutes; MS Calcd.: 416; MS Found: 417 ([M+1]$^+$).

Example 3

Synthesis of M-3pre 2-(2,6-Difluoro-4-((2-(4-(tributylstannyl)phenyl sulfonamide)ethyl)thio)phenoxy)acetamide (M-3pre) was synthesized in accordance with the following scheme. The $^1$H NMR spectrum of each compound was recorded with Bruker Avance III 400 MHz and Bruker Fourier 300 MHz by using TMS as an internal reference. The following one was used as LCMS: quadrupole mass spectrometer, Agilent LC/MSD 1200 series (column: ODS 2000 (50×4.6 mm, 5 μm) operated in ES (+) or (−) ionization mode; T=30° C.; flow rate=1.5 mL/min; detection wavelength: 254 nm.

[Chem. 27]
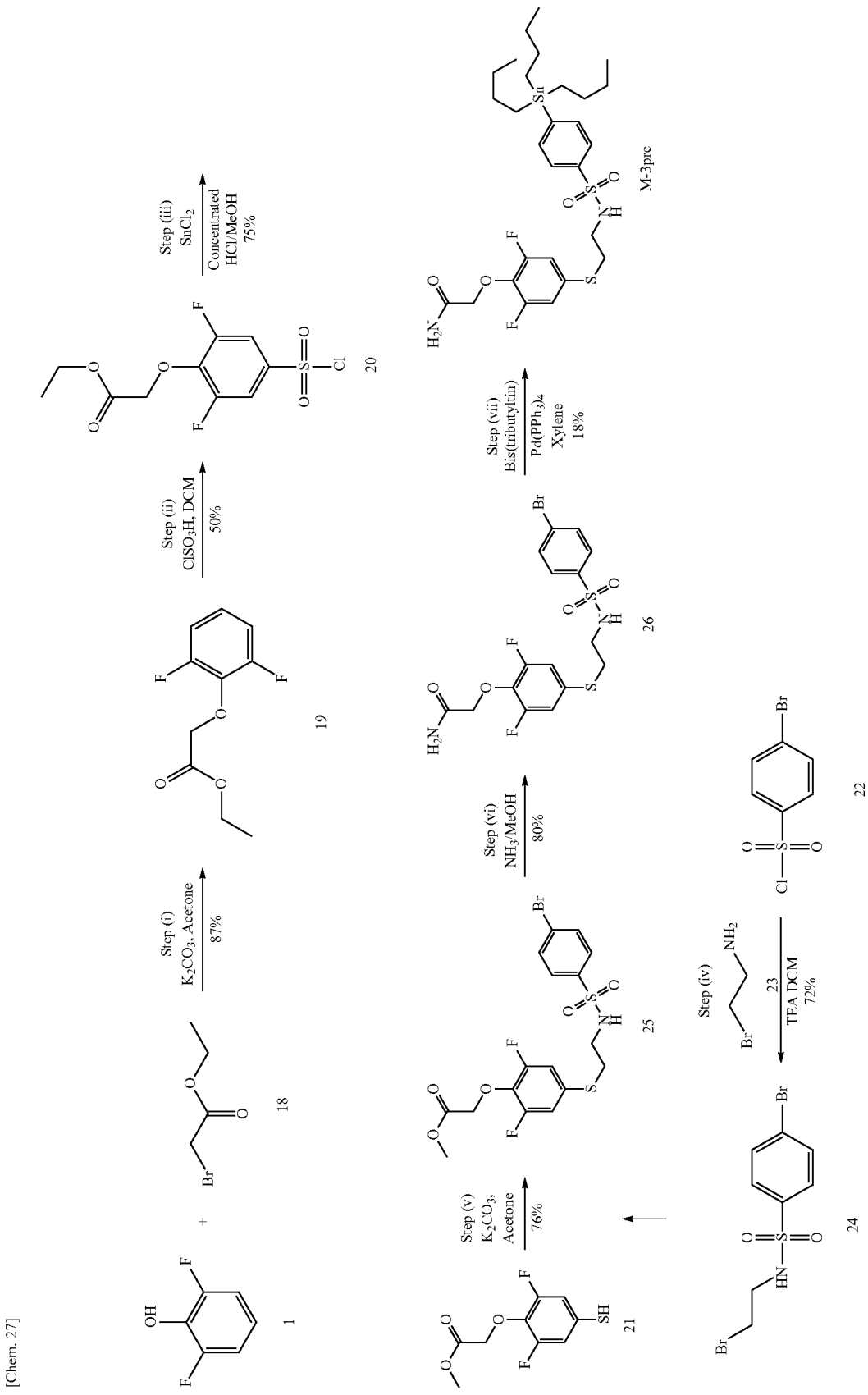

Step (i): Synthesis of ethyl 2-(2,6-difluorophenoxy)acetate (19)

[Chem. 28]

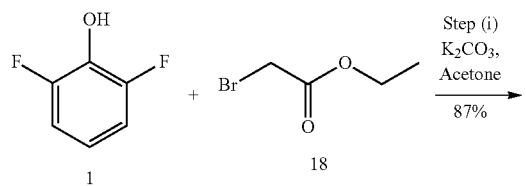

A mixture solution of the compound (1) (39.0 g, 0.30 mol), K₂CO₃ (62.0 g, 0.45 mol), the compound (18) (50.1 g, 0.30 mol), and acetone (200 mL) was stirred at room temperature for about 16 hours. The reaction mixture solution was poured to 3% HCl and extracted with ethyl acetate (90 mL×3). The combined organic layer was dried with sodium sulfate anhydride, filtered, and condensed. The residue was refined by silica gel column chromatography (PE: EA=10:1) to thereby obtain a compound (19) (57 g, 87%).

$^1$H NMR (CDCl$_3$, 300 MHz): δ 1.19 (t, J=7.2 Hz, 3H), 4.17 (q, J=7.2 Hz, 2H), 4.82 (s, 2H), 7.06-7.13 (m, 3H).

Step (ii): Synthesis of ethyl 2-(4-(chlorosulfonyl)-2,6-difluorophenoxy)acetate (20)

[Chem. 29]

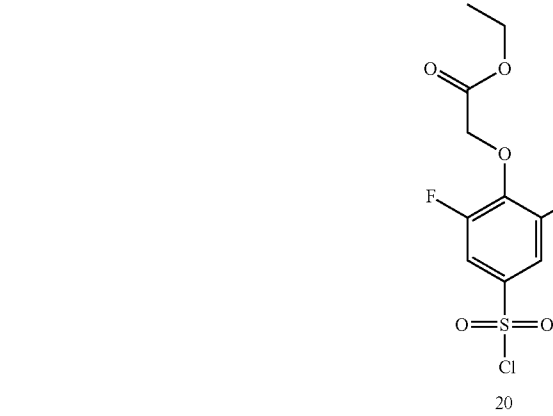

To a DCM (180 mL) solution of the compound (19) (50 g, 0.23 mol), ClSO₃H (106 mL, 1.38 mol) was added at 35° C. The reaction mixture solution was heated to reflux temperature and stirred for about 1.5 hours. Thereafter, the reaction mixture solution was poured to ice. The organic layer was separated, dried, and condensed, thereby obtaining a compound 20 (37 g, 50%).

$^1$H NMR (CDCl$_3$, 300 MHz): δ 1.18 (t, J=6.9 Hz, 3H), 4.16 (q, J=6.9 Hz, 2H), 4.83 (s, 2H), 7.18-7.21 (m, 2H).

Step (iii): Synthesis of methyl 2-(2,6-difluoro-4-mercaptophenoxy)acetate (21)

[Chem. 30]

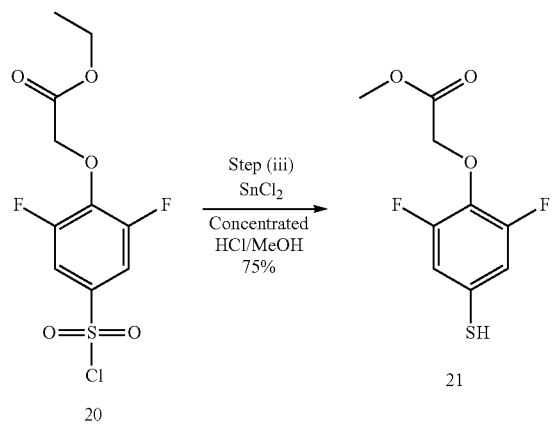

A mixture solution of the compound (20) (25.0 g, 0.08 mol), SnCl₂ (63.3 g, 0.28 mol), concentrated HCl (46.6 mL, 0.56 mol), and MeOH (333 mL) was heated to reflux temperature and stirred for about 1.5 hours. Thereafter, the reaction mixture solution was poured to ice and extracted with toluene. The organic layer was washed with 12% HCl three times, dried with sodium sulfate anhydride, and condensed. The residue was refined by silica gel column chromatography (PE:EA=2:1) to thereby obtain a compound (21) (14 g, 75%).

$^1$H NMR (CDCl$_3$, 300 MHz): δ 3.52 (s, 1H), 3.79 (s, 3H), 4.72 (s, 2H), 6.88 (d, J=6.3 Hz, 2H).

Step (iv): Synthesis of 4-bromo-N-(2-bromoethyl)benzenesulfonamide (24)

[Chem. 31]

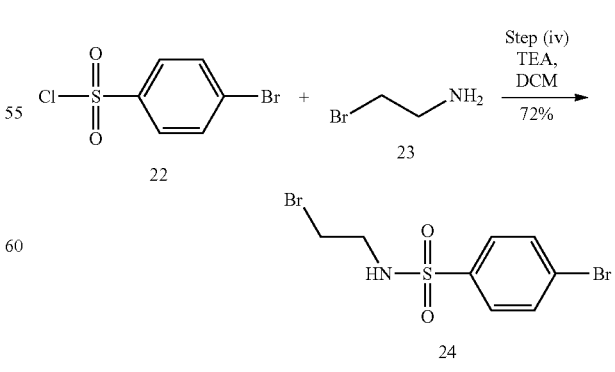

The compound (23) (1.35 g, 11.0 mmol) was added to a DCM (40 mL) solution of the compound (22) (2.54 g, 10.0 mmol), and subsequently, TEA (1.52 g, 15.0 mmol) was added thereto. Thereafter, the reaction mixture solution was stirred at room temperature for about 3 hours and diluted with water. The solution was extracted with DCM (80 mL×3). The organic layer was washed with brine, dried with sodium sulfate anhydride, and condensed. The crude product was refined by silica gel column chromatography (PE:EA=5:1) to thereby obtain a compound (24) (2.45 g, 72%).

$^1$H NMR (DMSO-d$_6$, 300 MHz): δ 3.12-3.16 (m, 2H), 3.43 (t, J=3.6 Hz, 2H), 7.69-7.73 (m, 2H), 7.79-7.82 (m, 2H), 8.13 (t, J=3.9 Hz, 1H).

Step (v): Synthesis of methyl 2-(4-((2-(4-bromophenyl sulfonamide)ethyl)thio)-2,6-difluorophenoxy)acetate (25)

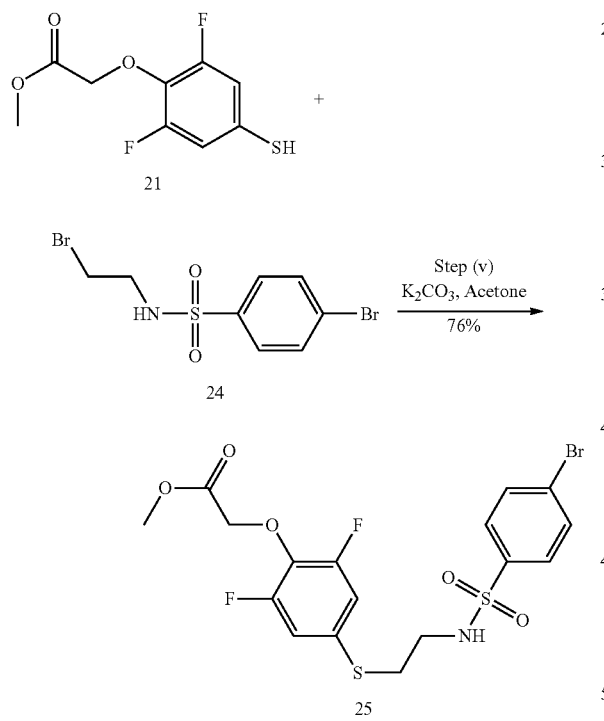

A mixture solution of the compound (21) (1.25 g, 5.36 mmol), K$_2$CO$_3$ (905 mg, 6.55 mmol), the compound (24) (1.88 g, 5.50 mmol), and acetone (50 mL) was stirred at room temperature for about 16 hours. The reaction mixture solution was poured to 3% HCl and extracted with ethyl acetate (90 mL×3). The organic layer was dried with sodium sulfate anhydride and condensed. The crude residue was refined by silica gel column chromatography (PE:EA=5:1) to thereby obtain a compound (25) (2 g, 76%).

$^1$H NMR (CDCl$_3$, 300 MHz): δ 2.94-2.98 (m, 2H), 3.08-3.14 (m, 2H), 3.77 (s, 3H), 4.73 (s, 2H), 5.33 (t, J=6.0 Hz, 1H), 6.78-6.84 (m, 2H), 7.61-7.70 (m, 4H).

Step (vi): Synthesis of 2-(4-((2-(4-bromophenyl sulfonamide)ethyl)thio)-2,6-difluorophenoxy)acetamide (26)

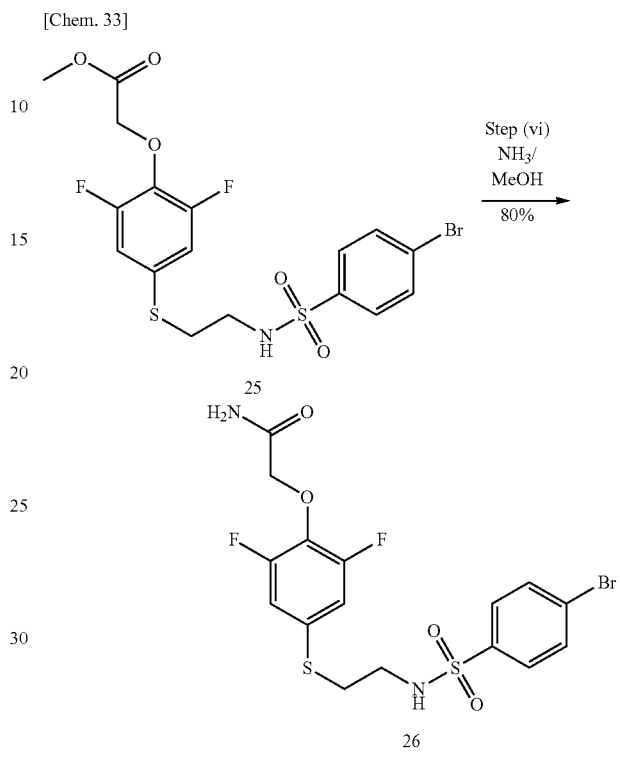

A mixture solution of the compound (25) (3.00 g, 6.06 mmol) and 2M NH$_3$/MeOH (150 mL, 300 mmol) was stirred at room temperature for about 16 hours. The obtained precipitate was recovered by filtration to thereby obtain a compound (26) (2.3 g, 80%).

$^1$H NMR (DMSO-d$_6$, 400 MHz): δ 2.93-2.96 (m, 2H), 3.00-3.03 (m, 2H), 4.48 (s, 2H), 7.10 (d, J=9.2 Hz, 2H), 7.40-7.45 (m, 2H), 7.70 (d, J=8.4 Hz, 2H), 7.80 (d, J=8.4 Hz, 2H), 8.01 (br s, 1H).

Step (vii): Synthesis of 2-(2,6-difluoro-4-((2-(4-(tributylstannyl)phenyl sulfonamide)ethyl)thio)phenoxy)acetamide (M-3pre)

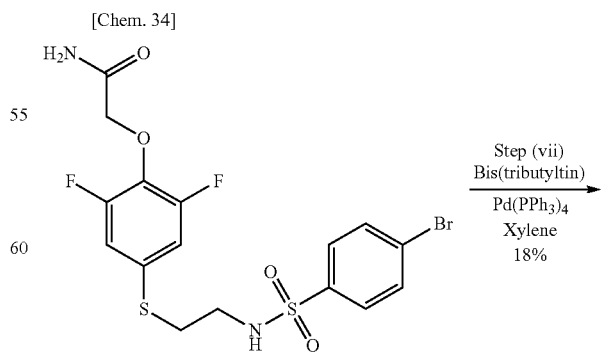

-continued

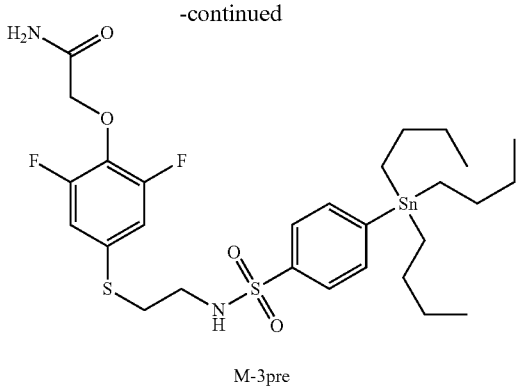

M-3pre

To a xylene (50 mL) solution of the compound (26) (670 mg, 1.39 mmol), bis(tributyltin) (0.87 mL, 1.81 mmol) and Pd(PPh$_3$)$_4$ (40 mg) were added. The reaction mixture solution was stirred under N$_2$ at 120° C. for about 1 hour. Thereafter, the reaction mixture solution was condensed under vacuum, and the residue was refined by silica gel column chromatography (PE:EA=3:1), thereby obtaining a compound (M-3pre) as yellow oil (180 mg, 18%).

$^1$H NMR (CD$_3$OD, 300 MHz): δ 0.94 (t, J=7.2 Hz, 9H), 1.12-1.17 (m, 5H), 1.29-1.39 (m, 8H), 1.52-1.60 (m, 5H), 2.98-3.06 (m, 4H), 4.55 (s, 2H), 7.01 (d, J=9.0 Hz, 2H), 7.68 (d, J=8.1 Hz, 2H), 7.77 (d, J=8.1 Hz, 2H); LCMS [mobile phase: 5% water (0.02% NH$_4$OAc) and 95% CH$_3$CN from 30% water (0.02% NH$_4$OAc) and 70% CH$_3$CN, 6 minutes, finally 0.5 minutes under these conditions] purity>95%, Rt=4.259 minutes; MS Calcd.: 692; MS Found: 693 ([M+H]$^+$).

Example 4

Synthesis of Radio-Labeled K-2

A radio-labeled K-2 was synthesized as follows.

[Chem. 35]

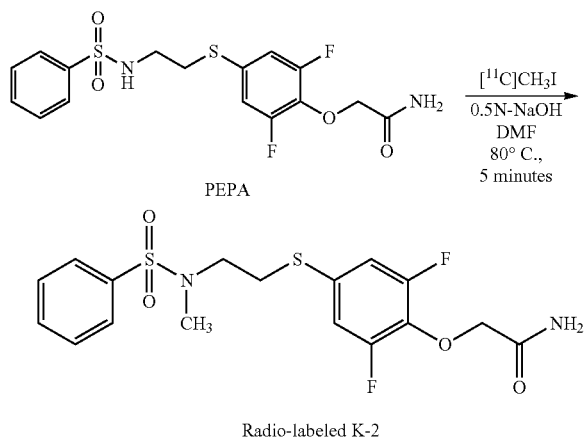

1 mg of PEPA (ca 2.5 μmol) was dissolved in DMF (0.3 mL), 0.5 N—NaOH aq (7 μL) was added thereto and mixed, and then the resultant mixture was charged into a reaction container in a hot cell. After [$^{11}$C]methyl iodide was collected with the normal method, the reaction was performed at 80° C. for 5 minutes. The resultant product was cooled to about room temperature, diluted with 500 μl of an LC solvent (CH$_3$CN:H$_2$O=1:1), and then subjected to LC separation. Capcell Pak UG-80 (10X250) (Shiseido Co., Ltd., Japan) was used as a column, separation was performed at a flow rate of 5.0 ml/min, and detection was performed using UV 254 nm and RI. The RI peak portion near about 8 minutes was separated and condensed under addition of Tween 80 (final concentration: 0.8%) and 2.5 mg of ascorbic acid using an evaporator. The residue was dissolved by adding 2.5 ml of physiological saline water.

The radio-labeled K-2 and the unlabeled K-2 were compared using HPLC. The HPLC analysis was developed using Capcell Pak UG-80 (4.6X250) (Shiseido Co., Ltd., Japan) at a flow rate of 1.0 ml/min, and detection was performed using UV 254 nm and RI. The unlabeled K-2 (UV detection) and the radio-labeled K-2 (RI detection) exhibited the same peak at a retention time of 8 minutes. This indicates that both are the same substance and the radio-labeled K-2 can be produced.

It was found that the reacted methyl iodide binds to sulfonamide of 100% PEPA, and it was found that the synthesis of the radio-labeled K-2 is extremely simple and exhibits a high yield.

Example 5

Synthesis of Radio-Labeled M-3

Pd$_2$(dba)$_3$ (1.74 mg), cuprous chloride (1.7 mg), and potassium carbonate (2.25 mg) were weighed in a 1-mL glass vial, and a DMF (300 μL) solution of P(o-tol)$_3$ (1.7 mg) was added to the mixture under a nitrogen atmosphere. The resultant mixture was stirred at room temperature for about 5 minutes, and then the solution was transferred to a labeling reaction container. [$^{11}$C]CH$_3$I was collected under cooling, and after radioactivity was saturated, a DMF solution (300 μL) of a tributyltin compound (preM-3) (1.6 mg) of a raw material was added thereto and the reaction was performed at 80° C. for about 5 minutes. The reaction mixture was allowed to pass through a PTFE filter to remove solid contents, HPLC separation was then performed, and the RI peak portion near about 7 minutes was separated, condensed, and compounded.

Pd$_2$(dba)$_3$: tris(dibenzylideneacetone)dipalladium
P(o-tolyl)$_3$: tri(o-tolyl)phosphine

Example 6

Biological Example (Preparation and Administration of AMPA Receptor-Binding Compound)

In the LC-MS/MS experiment, all of the synthesized compounds were dissolved in 100% DMSO so as to have a concentration of 2.5 mM, diluted with physiological saline water immediately before administration (PEPA (1.2 pmol/g), M-1 (12 pmol/g), K-2 (12 pmol/g), M-3 (60 pmol/g), and M-2 (240 pmol/g)), and administered by the parenteral route. In the electrophysiological experiment, PEPA and K-2 were dissolved in 100% DMSO so as to have a concentration of 150 mM, diluted with ACSF as a reflux liquid immediately before the experiment so as to have a concentration of 150 μM and then used. In the biochemical experiment and the PET blocking experiment, K-2 was dissolved in 50% DMSO so as to have a concentration of 2.5 mM and 25 mM, and then administered to a rat at an amount of administration of 1 μl/weight (g) by the parenteral route so as to be 0.5 mg/kg and 5 mg/kg.

Experimental Animal

All animal experiments were received deliberations approvals by Animal Ethics Committees of Yokohama City University and the National Institute of Radiological Sciences. As rats, 6 to 10-week-old adult male Sprague-Dawley rats (SD rats) (Charles River Laboratories International, Inc., Japan) were used.

The LC-MS/MS experiment and the biochemical experiment were performed after a rat was allowed to get to sleep by inhalation of isoflurane while anesthesia was maintained using a dedicate carburetor at a concentration of 1.5%. The compound was adjusted to have an amount of administration of 1 μl/weight (g). The cervical part of the rat was incised to expose the jugular vein, and then the compound was administered from the jugular vein under direct vision using an insulin syringe (TERUMO CORPORATION, Japan). After the administration of the compound, the rat was maintained under anesthesia for 15 minutes, and then, the brain was extracted. In the LC-MS/MS experiment, the hippocampus region was collected in a thickness of approximately 2 mm from the extracted whole brain using Brain matrix (ASI instruments, U.S.), the tissue weight thereof was measured, and then the hippocampus region was put into a 1.5-ml conical tube. In the biochemical experiment, an acute brain section including the hippocampus and having a thickness of 400 μm was produced from the extracted whole brain using a vibratome (VT1000; Leica, Germany).

LC-MS/MS Experiment

As for the preliminary reviewing of measurement conditions, an optimal dilution solvent and an optimal dilution magnification for each compound were determined using the hippocampal tissue (Table 4).

TABLE 4

| | Type of solvent to be suspended | Final dilution magnification | Centrifugation condition |
|---|---|---|---|
| PEPA | ×10 acn(0.1% FA) | ×10 | 16000 g × 16 min |
| M1 | ×20 FAfree acn | ×20 | 21880 g × 60 min |
| M2 | ×4 H2O/×2 acn/×3 MeOH | ×9 | 21880 g × 60 min |
| M3 | ×4 H2O/×2 acn/×3 MeOH | ×9 | 21880 g × 60 min |
| K2 | ×20 FAfree acn | ×20 | 21880 g × 60 min |

Preparation of administraion compound and preparation condition of collected tissue
*acn Acetonitrile, FA Formic acid MeOH, Methanol After the recovering of the sample, the solvent which had been preliminarily reviewed was added in a predetermined amount to the conical tube. The resultant product was suspended using a homogenizer pestle and sufficiently crushed using a handy sonicator (UR-20P; TOMY SEIKO CO., LTD., Japan). Thereafter, the resultant product was subjected to vortex, and centrifugation under each predetermined condition, and then the supernatant was recovered. The supernatant was diluted at a predetermined magnification immediately before the measurement in LC-MS/MS. The concentration of the compound contained in the hippocampal tissue was measured using liquid chromatography and a quadrupole mass spectrometer (UPLC-MS/MS, Aquity UPLC I-Class System, Xevo TQ-S, Nihon Waters K.K., Japan). In UPLC, a column having a size of 2.1 mm i.d.×100 mm 1.8 μm (HSS T3, Nihon Waters K.K., Japan) was used, the mobile phase condition for each compound was preliminarily reviewed (Table 5), and the concentrations of the compounds were measured under the conditions.

TABLE 5

| | Flow rate | Mobile phase 1 | Mobile phase2 | Mobile phase1:2 | Column injection amount(μl) |
|---|---|---|---|---|---|
| PEPA | 0.4 ml/min | 0.1% FA + 2 mM AA | Acn | 95:5 | 5 |
| M1 | 0.4 ml/min | 0.05% FA | 0.05% FA + Acn | 95:5 | 5 |
| M2 | 0.4 ml/min | 0.05% FA | 0.05% FA + Acn | 95:5 | 5 |
| M3 | 0.4 ml/min | 0.05% FA | 0.05% FA + Acn | 95:5 | 5 |
| K2 | 0.15 ml/min | 0.05% FA | 0.05% FA + Acn | 80:20 | 10 |

Measurement condition in LC/MS-MS of sample and composition and measurement condition of mobile phase
*asn Acetonitrile, FA Formic acid, AA Ammonium acetate In mass spectrometry, the MS method was prepared for each compound in advance by using a high-concentration compound (Table 6), decomposition was performed from parent ions to daughter ions according to the protocol, and the concentrations of the compounds were measured by using the MRM method. Further, as for the calibration curve used for the concentration measurement, those produced by decapitating a 6 to 10-week-old rat not administered with a pharmacological agent under anesthesia with isoflurane to recover the hippocampal tissue, and then adding each compound to the collected hippocampal tissue at a known concentration were used.

TABLE 6

| | Size of parent-daughter | Cone voltage | colligeon energy | Condition of ES |
|---|---|---|---|---|
| PEPA | 403.0957-218.0793 | 12 | 16 | ES+ |
| M1 | 416.9175-71.9881 | 40 | 23 | ES+ |
| | 416.9175-231.9908 | 40 | 15 | ES+ |
| | 416.9175-259.9643 | 40 | 13 | ES+ |
| M2 | 420.9513-57.9931 | 42 | 27 | ES+ |
| | 420.9513-217.9407 | 42 | 17 | ES+ |
| | 420.9513-245.9805 | 42 | 11 | ES+ |
| M3 | 416.8537-57.9930 | 38 | 25 | ES+ |
| | 416.8537-217.9415 | 38 | 17 | ES+ |
| | 416.8537-245.9793 | 38 | 11 | ES+ |
| K2 | 416.9813-57.9965 | 30 | 23 | ES+ |
| | 416.9813-217.9404 | 30 | 17 | ES+ |
| | 416.9813-245.9781 | 30 | 9 | ES+ |

Measurement condition of each compound in MS (Calculation of Tissue Accumulation Ratio of Compound)

As a result of optimization of the measurement condition for each compound, it was found that the amount of administration to living subjects and the dilution magnification at the time of measurement are different. Therefore, in order to represent the percentage of the administered compound accumulated in the hippocampus, % ID/g (percentage injected dose per gram tissue) was calculated using the following calculation formula:

% ID/g=measurement value (pM)×dilution magnification×10/concentration of compound administered (pmol/g)×weight (g)/tissue weight (mg)

Five types of compounds that have been known to bind to an AMPA receptor were administered to a rat from the tail vein, after 15 minutes from administration, the hippocampal tissue was collected, and the concentrations of the compounds accumulated therein were measured so that it was found that the accumulation of PEPA was highest. From this result, it was suggested that the transfer rate of PEPA from the inside of blood to the brain is highest. (FIG. 1). The capability of K-2 that is a methyl imparting body of PEPA to bind to a receptor other than binding regions of K-2 was exhaustively investigated with respect to 60 target receptors. As a result, it was suggested that specificity of PEPA is high rather than other receptors which may bind.

TABLE 7

| | Inhibition (%) | |
|---|---|---|
| Assay system | K-2 ($1 \times 10^{-7}$ mol/L) | Positive substance |
| Adenosine A1 (Human) | 5.29 | 99.73 (DPCPX) |
| α1A-Adrenergic | 0.21 | 100.00 (Prazosin) |
| α1B-Adrenergic | 0.00 | 100.00 (Prazosin) |
| α2A-Adrenergic (Human) | 8.77 | 100.00 (Rauwolscine) |
| α2B-Adrenergic (Human) | 5.83 | 100.00 (Rauwolscine) |
| α2C-Adrenergic (Human) | 5.82 | 100.00 (Rauwolscine) |
| β1-Adrenergic (Human) | 0.82 | 98.60 ((±)-Propranolol) |
| β2-Adrenergic (Human) | 3.39 | 100.00 ((±)-Propranolol) |
| Androgen | 0.57 | 97.66 (Testosterone) |
| Angiotensin AT1 (Human) | 1.52 | 100.00 (Angiotensin II) |
| Angiotensin AT2 (Human) | 1.05 | 100.00 (Angiotensin II) |
| Bradykinin B2 (Human) | 10.34 | 99.47 (HOE140) |
| Ca channel (Type L, Dihydropyridine) | 0.53 | 99.61 (Nitrendipine) |
| Ca channel (Type N) | 0.31 | 99.35 (ω-Conotoxin GVIA) |
| CRF1 (Human) | 1.37 | 100.00 (Urocortin human) |
| Dopamine D1 (Human) | 10.17 | 100.00 (R(+)-SCH-23390) |
| Dopamine D2 short (Human) | 5.33 | 100.00 ((+)-Butaclamol) |
| Dopamine transporter (Human) | 0.29 | 100.00 (GBR12909) |
| Estrogen | 2.83 | 100.00 (β-Estradiol) |
| Endothelin ETA (Human) | 1.81 | 100.00 (Endothelin-1 human) |
| Endothelin ETB (Human) | 0.00 | 100.00 (Endothelin-1 human) |
| GABA A (Agonist site) | 0.38 | 97.63 (Muscimol) |
| GABA A (BZ central) | 1.54 | 100.00 (Diazepam) |
| GABA B | 1.90 | 99.44 (GABA) |
| Glutamate (AMPA) | 1.74 | 100.00 ((S)-AMPA) |
| Glutamate (Kainate) | 1.68 | 100.00 (Kainic acid) |
| Glutamate (NMDA agonist site) | 0.57 | 100.00 (L-Glutamic acid) |
| Glutamate (NMDA glycine site) | 0.64 | 100.00 (MDL105,519) |
| Glutamate (NMDA phencyclidine site) | 5.02 | 100.00 ((+)-MK-801) |
| Glycine (Strychnine sensitive) | 8.46 | 100.00 (Strychnine) |
| Histamine H1 (Human) | 6.53 | 100.00 (Pyrilamine) |
| Histamine H2 (Human) | 0.79 | 100.00 (Cimetidine) |
| Histamine H3 (Human) | 0.00 | 98.17 ((R)(−)-α-Methyl histamine) |
| K Channel KATP | 5.71 | 100.00 (Glybenclamide) |
| K Channel SKCa | 0.00 | 99.94 (Apamin) |
| Leukotriene B4 | 0.00 | 98.89 (Leukotriene $B_4$) |
| Leukotriene D4 | 0.16 | 100.00 (Leukotriene $D_4$) |
| Melatonin MT1 (Human) | 0.11 | 100.00 (Melatonin) |
| Muscarinic M1 (Human) | 2.24 | 99.68 (Atropine) |
| Muscarinic M2 (Human) | 0.51 | 99.80 (Atropine) |
| Muscarinic M3 (Human) | 5.99 | 99.84 (Atropine) |
| Na channel site 2 | 11.15 | 97.37 (Dibucaine) |
| Neurokinin NK1 (Human) | 0.00 | 94.45 (L-703,606) |
| Neurokinin NK2 (Human) | 0.61 | 100.00 (Neurokinin A) |
| Neurokinin NK3 (Human) | 0.00 | 98.43 (Senktide) |
| Norepinephrine transporter (Human) | 0.00 | 96.22 (Desipramine) |
| Nicotinic (Human) | 7.17 | 98.46 ((±)-Epibatidine) |
| Opiate δ (Human) | 0.30 | 98.32 (Naltriben) |
| Opiate κ (Human) | 0.00 | 100.00 (U-69593) |
| Opiate μ (Human) | 8.78 | 99.30 (DAMGO) |
| PAF | 0.00 | 99.83 (PAF) |
| Serotonin 5HT1A (Human) | 1.98 | 98.31 (Serotonin) |
| Serotonin 5HT2A (Human) | 9.32 | 99.20 (Ketanserin) |
| Serotonin 5HT3 (Human) | 1.57 | 99.80 (Tropisetron) |
| Serotonin transporter (Human) | 0.17 | 100.00 (Imipramine) |
| Sigma σ1 | 2.88 | 100.00 ((+)-Pentazocine) |
| Sigma σ2 | 4.07 | 100.00 (Haloperidol) |
| Vasopressin V1 | 4.76 | 100.00 ([$Arg^8$]-Vasopressin) |
| Vasopressin V1B (Human) | 1.48 | 99.69 ([$Arg^8$]-Vasopressin) |
| VIP 1 (Human) | 0.00 | 97.98 (VIP) |

Electrophysiological Experiment

A 7- to 8-week-old male SD rat was used. The rat was decapitated under anesthesia with isoflurane, and an acute brain section including the hippocampus and having a thickness of 400 μm was produced using a vibratome (VT1000; Leica, Germany). The section was left to stand still in ACSF at room temperature for 60 minutes, and then the AMPA current was measured by a whole-cell recording method. 100 μM of picrotoxin and 100 μM of DL-APV were administered under the condition that the ACSF was refluxed at a rate of 3 ml/min, and then only the AMPA current was isolated and measured.

The recording electrode was placed on a pyramidal cell in CA1, and the exciting electrode was placed on the Schaffer fiber separated away from the recording cell by 100 to 200 μm. The whole cell recording was performed by fixing the voltage of the cell membrane to −80 mV and applying stimulation of 100 microseconds at a frequency of every 30 seconds. The AMPA current in the ground state was recorded for 5 minutes, reflux was thereafter performed using ACSF added with PEPA or K-2 for 15 minutes, and then the AMPA current was recorded in the reflux liquid not containing PEPA or K-2 for 30 minutes.

At the time of standing still and refluxing the brain section, typically, ACSF was saturated with 95% $O_2$/5% $CO_2$ and then used. The composition of ACSF is as follows; 119 mM NaCl, 2.5 mM KCl, 2.5 mM $CaCl_2$, 1.5 mM $MgSO_4$, 26 mM $NaHCO_3$, and 1 mM $NaH_2PO_4$. The recording electrode was produced by using a glass tube (GD-1.5; NARISHIGE Group, Japan) and adjusting the tip resistance to 3 to 5 MOhm and then used. The composition of the filling liquid in the recording electrode is as follows; 115 mM $CsMeSO_4$, 20 mM CsCl, 10 mM HEPES, 2.5 mM $MgCl_2$, 4 mM $Na_2ATP$, 0.4 mM $Na_3GTP$, 10 mM Na-phosphocreatinine, and 0.6 mM EGTA. The result was represented by an average value of the AMPA current for final 10 minutes among the AMPA currents recorded for 30 minutes after the administration of the pharmacological agent when an average value of the AMPA current in the ground state for 5 minutes was converted as 1.

Biological Experiment

Hippocampus membrane surface fraction—a 7- to 8-week-old male SD rat was used. K-2 or 50% DMSO was administered by the parenteral route under anesthesia with isoflurane, and after 15 minutes, the rat was decapitated. An acute brain section including the hippocampus and having a thickness of 400 μm was produced using a vibratome, and the section was left to stand still in ACSF at room temperature for 60 minutes. Subsequently, in order to biotinylate the membrane surface protein, only the hippocampus section was extracted from the acute brain section, and the section was slowly stirred at 4° C. for 45 minutes in ACSF containing 2.0 mg/ml of biotin (EZ Link Sulfo-NHS-Biotin; Thermo Scientific, U.S.). After the biotinylation, the section was rinsed with 1 ml of ice-chilled TBS at pH 7.5 five times, and suspended by a pestle in 150 μl of homogenization buffer (150 mM NaCl, 0.5 mM EDTA, 0.1 mM EGTA, 1 mM HEPES, 20% Triton X100). Further, 150 μl of homogenization buffer was added thereto and then the resultant product was subjected to ultrasonic fragmentation using a handy sonicator. Thereafter, centrifugal separation was performed at 4° C. for 15 minutes at 14,000×g, and then the supernatant (up to 300 μl) was recovered. The homogenization of the protein concentration of the supernatant was performed with protein quantitative determination, 50 μl of the supernatant was then mixed with 10 μl of 6× sample buffers, and the resultant mixture was heated at 100° C. for 5 minutes to recover the total protein fraction (total fraction). Further, in order to immunoprecipitate the biotinylated surface protein, 150 μl of the remaining supernatant was mixed with 150 μl of NeutrAvidin agarose resin (Thermo Scientific, U.S.), and then the resultant mixture was stirred at 4° C. for 16 hours. Thereafter, centrifugation was performed at 4° C. for 1 minute at 2,000×g to discard the supernatant, and the remaining beads were rinsed with 1000 μl of IP buffer five times. Subsequently, 150 μl of 2× sample buffers were added thereto, the resultant product was heated for 5 minutes, and then the supernatant was recovered, thereby obtaining the membrane protein fraction (surface fraction).

Quantitative Western blot—the total protein fraction and the membrane protein fraction were subjected to electrophoresis using polyacrylamide gel (Mini-PROTEAN TGX precast Gel; Bio-rad, U.S.) and then transferred to the PVDF membrane. The membrane was treated for 1 hour using a blocking solution produced by a blocking agent (Perfectblock; Mobitec, U.S.)/TBS-T (137 mM NaCl, 2.68 mM KCl, 25 mM Tris, 0.1% Triton-X, PH 7.6). As for the primary antibody, Pan AMPA antibody/GluA2/3/4 rabbit antibody (1:1000, cell signaling technology, U.S.) and GAPDH antibody for confirming that intracellular fractions are not mixed in the membrane protein fractions (1:1000, cell signaling technology) were used, diluted with a blocking solution at a ratio of 1:1000, and subjected to reaction at room temperature for 1 hour and 3 hours, respectively. Thereafter, the primary antibody was washed with TBS-T for 10 minutes three times, and then subjected to reaction with the anti-rabbit secondary antibody (1:1000; Jackson ImmunoResearch, U.S.) at room temperature for 1 hour. Subsequently, the resultant product was washed with TBS-T for 10 minutes three times, and a band was detected using amersham ECL (GE Healthcare Japan, Japan) by a chemiluminescence photographic apparatus (LAS4000 mini; GE). The signal intensity of the obtained band was quantitatively analyzed by Multi Gauge V3.0 (FUJIFILM Corporation, Japan).

(In Vivo PET Imaging Using Rat)

The PET imaging was performed using micro PET (Focus 220; Siemens Medical Solution). PET imaging experiment using a rat: After the rat was allowed to get to sleep by isoflurane (DS Pharma Animal Health Co., Ltd., Japan), anesthesia was maintained at an isoflurane concentration of 1.5% (air 2 L/min), and then the intravenous line was secured from the tail vein by a 24G Surflo indwelling needle (TERUMO CORPORATION, Japan). The rat was fixed to the PET imaging base, and then radiation imaging for checking the position was performed before imaging. Thereafter, 50% DMSO or K-2 dissolved in 50% DMSO was administered by the parenteral route, and after 3 minutes from administration, the radio-labeled K-2 (about 4 MBq) was administered. During the PET imaging, the body temperature was maintained to 37±0.5° C. using a feedback type heating plate (BWT-100A; Bio Research Center, Japan). After the imaging, the intravenous line was removed, the administration of isoflurane was stopped, and then the rat was removed from the PET imaging base and returned to the home cage. The rat was raised in the room in which imaging was performed during 1 week after the imaging, and then the rat was returned to the normal rat group rearing room.

A summation image was constructed and offset was removed therefrom with a 0.5-mm Hanning filter so as to reconstruct a dynamic image. The reconstructed image was analyzed using PMOD image analysis software (PMOD technologies) by combining VOIs including a plurality of regions of the striatum, the hippocampus, the cerebellum, the brain stem, and the like with a region formed on the template MRI image. The calculation value used in quantitative determination was % SUV (% of standardized uptake value) and obtained by the following formula;

% SUV=amount of radiation of each tissue surrounded by VOI (MBq)/administered amount of radiation (MBq)×weight (g)

Experimental Result (Characteristic Evaluation of AMPA Receptor-Recognizing Compound)

In order to evaluate the binding characteristics of the synthesized compounds to an AMPA receptor, analysis was performed using electrophysiological and biochemical techniques. Using the acute hippocampus section produced from the adult rat, it was confirmed that the AMPA current is significantly increased by the administration of PEPA for 15 minutes (2.4±0.13, n=4 from four animals; p=0.01 vs reference). Further, the same experiment was performed using K-2, and it was confirmed that the AMPA current is significantly increased also in the case of K-2 (1.7±0.22, n=5 from four animals; p=0.01 vs reference) (FIG. 2).

Next, the mechanism of increasing the AMPA current was biochemically reviewed. A brain section including the hippocampus was produced from the rat whose living organism was administered with K-2, and the AMPA receptor presented on the surface of the cell membrane was quantitatively determined by a biotinylation method. As a result, the transfer of the AMPA receptor to the membrane surface was promoted by administration of 5 mg/kg of K-2 (136%±14, n=5 from five animals; p=0.05 vs 50% DMSO). On the other hand, a change in the total amount of the AMPA receptors in the same animal was not recognized (FIG. 3). From the above results, it was found that K-2 causes the surface presentation amount of the AMPA receptor to be acutely increased.

(PET Imaging in Rat by Using AMPA Receptor-Recognizing Compound K-2)

It was clearly recognized that K-2 exhibited binding to the AMPA receptor, and thus, the radio-labeled K-2 was then administered to the rat and the PET imaging in vivo was performed. As a result, the radio-labeled K-2 in the rat exhibited extremely high brain uptake and was specifically accumulated in a region that includes the hippocampus, the striatum, and the cerebellum and is known that a large number of AMPA receptors histologically exist (left in FIG. 4 and (a) in FIG. 5).

Next, in order to review the specificity of K-2 accumulation, the blocking experiment to administer non-radio-labeled K-2 was performed 3 minutes before the administration of radio-labeled K-2. By prior administration of 0.5 mg/kg of non-radio-labeled K-2, it was clearly recognized that the specific accumulation of radio-labeled K-2 is lost and K-2 specifically binds to the AMPA receptor in vivo (right in FIG. 4 and (b) in FIG. 5).

Further, the degree of loss of specific binding was small in the case of the prior administration of 0.05 mg/kg of non-radio-labeled K-2, as compared to the case of the prior administration of 0.5 mg/kg of K-2, and as a result, concentration dependency in blocking was exhibited and saturated binding was suggested (FIG. 6). The uptake of the brain stem was not changed by blocking, and thus it is found that the expression of the AMPA receptor in this region is less ((c) and (d) in FIG. 5). Therefore, when an uptake ratio of the radio-labeled K-2 in the hippocampus was calculated using the brain stem as a reference portion, it was found that high specific binding was exhibited in 20 to 60 minutes after the administration of the radio-labeled K-2 (FIG. 7). The specific binding was quantified by the Logan Plot method (FIG. 8). BPnd (estimated binding potential) was significantly lowered by blocking using the non-radio-labeled K-2 (gray in FIG. 8). Further, it was clearly recognized that a value representing specific binding (black in FIG. 8) has a high correlation with a value obtained by biochemically measuring the total expression level of the AMPA receptor in the tissue (FIG. 9), and the in vivo PET imaging reflects the distribution of the AMPA receptors. Further, the biochemical expression level (crude fractionation) of the AMPA receptor in each brain region and the PET image value in the same region exhibit a high correlation (FIG. 10).

shRNA can specifically suppress the expression of a specific protein. shRNA that can suppress the expression of AMPA receptors (GluA1 to 3) was caused to be expressed at the left striatum by using lentivirus, and scramble RNA that is non-functional shRNA was caused to be expressed at the right striatum. As a result, in the in vivo PET image, a decrease in uptake of the radio-labeled K-2 at the shRNA side was recognized (FIG. 11). Further, a decrease in the PET image value in seven rats actually was about 30% (FIG. 12). From this result, the radio-labeled K-2 exhibited high specificity with respect to the AMPA receptor in living subjects.

Description of Abbreviations

ACSF: artificial cerebrospinal fluid
AMPA: α-amino-3-hydroxy-5-methyl-4-isoxazole-propionic acid
DIPEA: diisopropylethylamine
DCM: dichloromethane
EA: ethyl acetate
PE: petroleum ether
PEPA: 2-[2,6-difluoro-4-({2-[(phenylsulfonyl)amino]ethyl}thio)phenoxy]acetamide
PET: positron emission tomography
TEA: tetraethylammonium
TMS: tetramethylsilane
1-BCP: 1-(1,3-benzodioxol-5-ylcarbonyl)-piperidine
SYM 2206: (±)-4-(4-aminophenyl)-1,2-dihydro-1-methyl-2-propylcarbamoyl-6,7-methylenedioxyphthalazine
GYKI: 4-(8-methyl-9H-[1,3]dioxolo[4,5-h][2,3]benzodiazepin-5-yl)aniline
CX546: 2,3-dihydro-1,4-benzodioxin-7-yl-(1-piperidyl)methanone

The invention claimed is:

1. A compound of Formula (I), or a pharmaceutically acceptable salt thereof or solvate thereof:

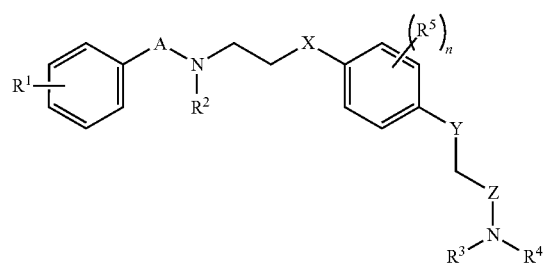

Formula (I)

wherein:
each of A and Z independently is CO, SO, or $SO_2$;
each of X and Y independently is S or O;

each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo; and
n is an integer of 0 to 4.

2. The compound or pharmaceutically acceptable salt thereof or solvate thereof according to claim 1, wherein each of A and Z independently is CO or $SO_2$.

3. The compound or pharmaceutically acceptable salt thereof or solvate thereof according to claim 1, wherein A is $SO_2$ and Z is CO.

4. The compound or pharmaceutically acceptable salt thereof or solvate thereof according to claim 1, wherein X is S and Y is O.

5. The compound or pharmaceutically acceptable salt thereof or solvate thereof according to claim 1, wherein $R^2$ is alkyl.

6. The compound or pharmaceutically acceptable salt thereof or solvate thereof according to claim 1, wherein $R^1$ is alkyl or halo.

7. The compound or pharmaceutically acceptable salt thereof or solvate thereof according to claim 1, wherein one of $R^3$ and $R^4$ is hydrogen and the other one is alkyl.

8. The compound or pharmaceutically acceptable salt thereof or solvate thereof according to claim 1, wherein $R^5$ is halo.

9. The compound or pharmaceutically acceptable salt thereof or solvate thereof according to claim 8, wherein $R^5$ is fluoro.

10. The compound or pharmaceutically acceptable salt thereof or solvate thereof according to claim 1, wherein n is 2.

11. The compound or pharmaceutically acceptable salt thereof or solvate thereof according to claim 1, wherein the compound is

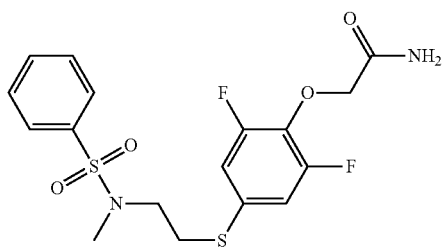 [SMILES: CN(CCSc1cc(F)c(OCC(N)=O)c(F)c1)S(=O)(=O)c1ccccc1]

and pharmaceutically acceptable salts thereof and solvates thereof.

12. A compound of Formula (I), or a pharmaceutically acceptable salt thereof or solvate thereof:

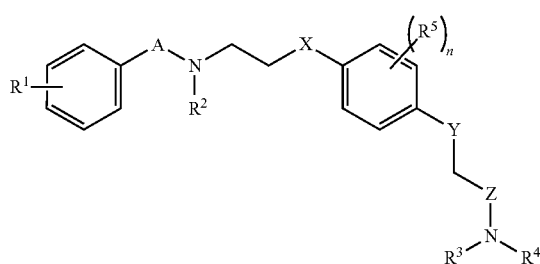

Formula (I)

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo;
n is an integer of 0 to 4; and one or more atoms are a radioisotope of the atom or atoms.

13. The compound according to claim 12, or the pharmaceutically acceptable salt thereof or solvate thereof, wherein the radioisotope is $^{11}C$ or $^{18}F$.

14. The compound according to claim 13, or the pharmaceutically acceptable salt thereof or solvate thereof, wherein a group containing a radioisotope is $R^1$.

15. The compound according to claim 13, or the pharmaceutically acceptable salt thereof or solvate thereof, wherein a group containing a radioisotope is $R^2$.

16. The compound according to claim 13, or the pharmaceutically acceptable salt thereof or solvate thereof, wherein a group containing a radioisotope is at least one of $R^3$ and $R^4$.

17. The compound according to claim 13, selected as:

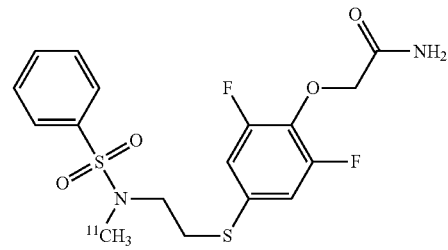 [SMILES: [11CH3]N(CCSc1cc(F)c(OCC(N)=O)c(F)c1)S(=O)(=O)c1ccccc1]

and pharmaceutically acceptable salts thereof and solvates thereof.

18. A composition comprising the compound according to claim 1, or the pharmaceutically acceptable salt thereof or solvate thereof.

19. A method for imaging an α-amino-3-hydroxy-5-methyl-4-isoxazole-propionic acid (AMPA) receptor in the brain of a living subject who has been administered a composition comprising a compound of Formula (I) or pharmaceutically acceptable salt thereof or solvate thereof:

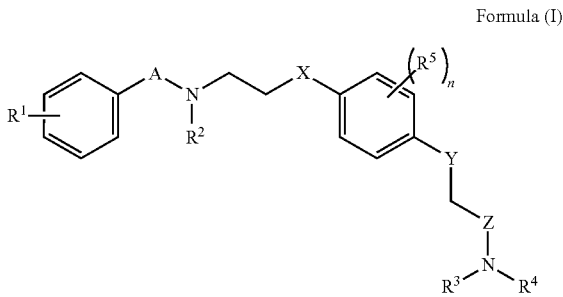

Formula (I)

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;

each $R^5$ independently is alkyl, alkenyl, alkynyl, or halo; and n is an integer of 0 to 4; and one or more atoms are a radioisotope of the atom or atoms, the method comprising imaging the AMPA receptor in the brain of the living subject.

20. The method according to claim 19, wherein the composition is used for molecular imaging.

21. A method for imaging an α-amino-3-hydroxy-5-methyl-4-isoxazole-propionic acid (AMPA) receptor in the brain of a living subject who has been administered a composition comprising a compound of Formula (I), or a pharmaceutically acceptable salt thereof or solvate thereof:

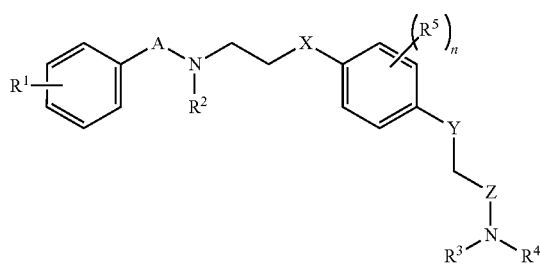

Formula (I)

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo; and
n is an integer of 0 to 4, the method comprising imaging the AMPA receptor in the brain of the living subject.

22. A method for producing a compound of Formula (I), or a pharmaceutically acceptable salt thereof or solvate thereof:

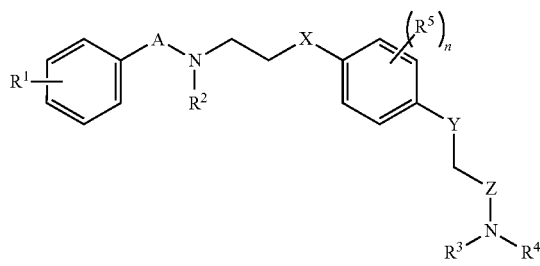

Formula (I)

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo; and
n is an integer of 0 to 4, the method comprising reacting a compound of Formula (II), or a pharmaceutically acceptable salt thereof or solvate thereof:

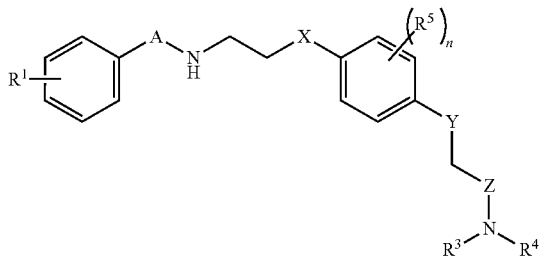

Formula (II)

wherein,
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
each $R^5$ independently isrep18sems alkyl, alkenyl, alkynyl, or halo; and
n is an integer of 0 to 4,
with $X^1$—$R^2$, wherein $R^2$ is alkyl, alkenyl, or alkynyl and $X^1$ is halogen.

23. The method according to claim 22, wherein $R^2$ is [$^{11}$C]alkyl.

24. The method according to claim 22, wherein both $R^3$ and $R^4$ in Formula (I) and Formula (II) are hydrogen.

25. A method for imaging an α-amino-3-hydroxy-5-methyl-4-isoxazole-propionic acid (AMPA) receptor in the brain of a living subject, the method comprising a step of detecting radiation emitted from the brain in a living subject to which a compound of Formula (I), or a pharmaceutically acceptable salt thereof or solvate thereof, has been administered:

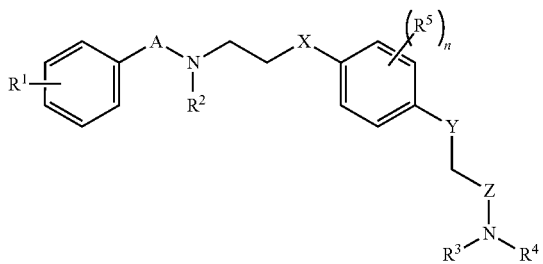

Formula (I)

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo;
n is an integer of 0 to 4; and
one or more atoms are a radioisotope of the atom or atoms.

26. A method for imaging an α-amino-3-hydroxy-5-methyl-4-isoxazole-propionic acid (AMPA) receptor in the brain of a living subject, the method comprising the step of administering to the subject a composition comprising a compound of Formula (I), or pharmaceutically acceptable salt thereof or solvate thereof:

Formula (I)

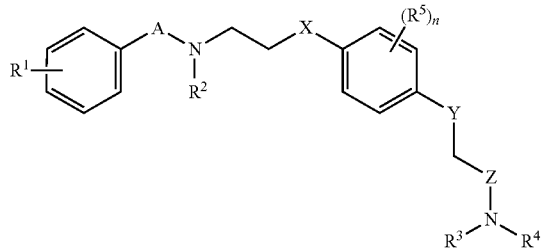

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo;
n is an integer of 0 to 4; and
one or more atoms are a radioisotope of the atom or atoms; and imaging the AMPA receptor in the brain of the living subject.

27. A method for imaging an α-amino-3-hydroxy-5-methyl-4-isoxazole-propionic acid (AMPA) receptor in the brain of a living subject, the method comprising the step of administering to the subject a composition comprising a compound of formula (I), or a pharmaceutically acceptable salt thereof or solvate thereof:

Formula (I)

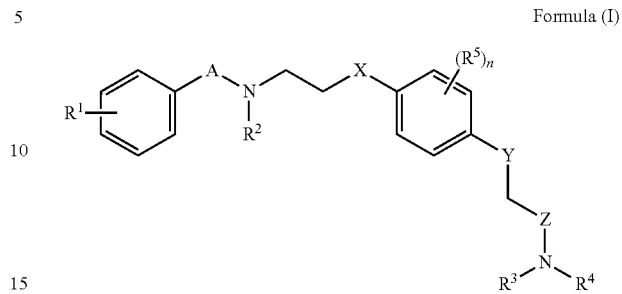

wherein:
each of A and Z independently is CO, SO, or $SO_2$;
each of X and Y independently is S or O;
each of $R^1$, $R^3$, and $R^4$ independently is hydrogen, alkyl, alkenyl, alkynyl, or halo;
$R^2$ is alkyl, alkenyl, or alkynyl;
each $R^5$ independently is alkyl, alkenyl, alkynyl, or halo; and
n is an integer of 0 to 4; and imaging the AMPA receptor in the brain of the living subject.

* * * * *